US007871619B2

(12) United States Patent
Burns et al.

(10) Patent No.: US 7,871,619 B2
(45) Date of Patent: Jan. 18, 2011

(54) COMPOSITIONS AND METHODS FOR DETECTING AND TREATING DISEASES AND CONDITIONS RELATED TO CHEMOKINE RECEPTORS

(75) Inventors: Jennifer M. Burns, San Mateo, CA (US); Bretton Summers, Redwood City, CA (US); Maureen C. Howard, Los Altos, CA (US); Thomas J. Schall, Palo Alto, CA (US); Zhenhua Miao, San Jose, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 1208 days.

(21) Appl. No.: 10/912,638

(22) Filed: Aug. 4, 2004

(65) Prior Publication Data
US 2005/0074826 A1 Apr. 7, 2005

Related U.S. Application Data

(63) Continuation-in-part of application No. 10/698,541, filed on Oct. 30, 2003, now Pat. No. 7,253,007, which is a continuation-in-part of application No. 10/452,015, filed on May 30, 2003, now Pat. No. 7,413,866, which is a continuation-in-part of application No. 10/245,850, filed on Sep. 16, 2002, now Pat. No. 7,442,512.

(60) Provisional application No. 60/338,100, filed on Nov. 30, 2001, provisional application No. 60/337,961, filed on Nov. 30, 2001, provisional application No. 60/434,912, filed on Dec. 20, 2002.

(51) Int. Cl.
*A61K 39/395* (2006.01)
*A61K 39/44* (2006.01)
*C12P 21/08* (2006.01)
*C07K 16/28* (2006.01)

(52) U.S. Cl. .............. 424/143.1; 424/142.1; 424/130.1; 512/12; 530/387.1

(58) Field of Classification Search ........................ None
See application file for complete search history.

(56) References Cited

U.S. PATENT DOCUMENTS

| 4,166,452 | A | 9/1979 | Generales, Jr. |
| 4,256,108 | A | 3/1981 | Theeuwes |
| 4,265,874 | A | 5/1981 | Bonsen et al. |
| 4,927,838 | A | 5/1990 | Guthrie et al. |
| 5,994,519 | A | 11/1999 | Osbourn et al. |
| 6,084,075 | A | 7/2000 | Lind et al. |
| 6,140,064 | A | 10/2000 | Loetscher et al. |
| 6,156,520 | A | 12/2000 | Inglese et al. |
| 6,180,336 | B1 | 1/2001 | Osbourn et al. |
| 6,184,358 | B1 | 2/2001 | Loetscher et al. |
| 6,197,069 | B1 | 3/2001 | Poste et al. |
| 6,329,159 | B1 | 12/2001 | Andrew et al. |
| 6,365,356 | B1 | 4/2002 | Gershengorn |
| 6,448,054 | B1 | 9/2002 | Poznansky et al. |
| 6,537,764 | B1 | 3/2003 | Gerard et al. |
| 2002/0004215 | A1 | 1/2002 | Osbourn et al. |
| 2002/0025536 | A1 | 2/2002 | Gyuris et al. |
| 2002/0034757 | A1 | 3/2002 | Cubicciotti |
| 2002/0037539 | A1 | 3/2002 | Qin et al. |
| 2002/0048786 | A1 | 4/2002 | Rosen et al. |
| 2002/0061599 | A1 | 5/2002 | Elling et al. |
| 2002/0061834 | A1 | 5/2002 | Rosen et al. |
| 2002/0064770 | A1 | 5/2002 | Nestor, Jr. et al. |
| 2002/0076710 | A1 | 6/2002 | Papsidero et al. |

FOREIGN PATENT DOCUMENTS

| EP | 0897980 A2 | 2/1999 |
| WO | WO 98/11218 A1 | 3/1998 |
| WO | WO 98/14480 A1 | 4/1998 |
| WO | WO 99/50461 A1 | 10/1999 |

OTHER PUBLICATIONS

Ebert, Lisa M. et al.; "Coregulation of CXC Chemokine Receptor and CD4 Expression on T Lymphocytes During Allogeneic Activation"; 2001, *Journal of Immunology*, vol. 166, No. 8, pp. 4870-4878.
Abdel-Magid, Ahmed F. et al.; "Reductive Amination of Aldehydes and Ketones by Using Sodium Triacetoxyborohydride"; *Tetrahedron Lett.*, 1990, vol. 31, pp. 5595-5598.
Babcock, Gregory J. et al.; "Ligand Binding Characteristics of CXCR4 Incorporated into Paramagnetic Proteoliposomes"; *The Journal of Biological Chemistry* 2001, vol. 276 No. 42, pp. 38433-38440.
Baribaud, Frederic et al.; "Antigenically Distinct Conformations of CXCR4"; *Journal of Virology* 2001, vol. 75 No. 19, pp. 8957-8967.
Barney, Charlotte L. et al.; "A Convenient Synthesis of Hindered Amines and α-Trifluoromethylamines from Ketones"; *Tetrahedron Lett.*, 1990, vol. 31, pp. 5547-5550.
Bertolini, Francesco et al.; "Endostatin, an antiangiogenic drug, induces tumor stabilization after chemotherapy or anti-CD20 therapy in a NOD/SCID mouse model of human high-grade non-Hodgkin lymphoma"; *Blood*, 2000, vol. 96, No. 1, pp. 282-287.
Bertolini, Francesco et al.; "CXCR4 Neutralization, a Novel Therapeutic Approach for Non-Hodgkin's Lymphoma"; *Cancer Research*, 2002, vol. 62, pp. 3106-3112.
Cook, Jonathan S. et al.; "Characterization of the RDC1 gene which encodes the canine homolog of a proposed human VIP receptor"; 1992, FEBS Letters, vol. 300, No. 2, pp. 149-152.
Dairaghi, Daniel J.; "HHV8-encoded vMIP-I Selectively Engages Chemokine Receptor CCR8"; *The Journal of Biological Chemistry* 1999, vol. 274, No. 31, pp. 21569-21574.
Dragic, Tatjana; "An overview of the determinants of CCR5 and CXCR4 co-reseptor function"; *Journal of General Virology* 2001, vol. 82, pp. 1807-1814.

(Continued)

*Primary Examiner*—Bridget E Bunner
*Assistant Examiner*—Fozia M Hamud
(74) *Attorney, Agent, or Firm*—Townsend and Townsend and Crew LLP

(57) ABSTRACT

Ligands of CCX-CKR2 and the biological role of CCX-CKR2 in cancer is described.

10 Claims, 16 Drawing Sheets

OTHER PUBLICATIONS

Forster, Reinhold et al.; "Intracellular and Surface Expression of the HIV-1 Coreceptor CXCR4/Fusin on Various Leukocyte Subsets: Rapid Internalization and Recycling Upon Activation"; *The Journal of Immunology* 1998, vol. 160, pp. 1522-1531.

Gerlach, Lars Ole et al.; "Molecular Interactions of Cyclam and Bicyclam Non-peptide Antagonists with the CXCR4 Chemokine Receptor"; *The Journal of Biological Chemistry* 2001, vol. 276 No. 17, pp. 14153-14160.

Gosling, Jennifa et al.; "Cutting Edge: Identification of a Novel Chemokine Receptor That Binds Dendritic Cell- and T Cell-Active Chemokines Including ELC, SLC, and TECK"; *The Journal of Immunology* 2000, pp. 2851-2856.

Gribble, Gordon, W. et al.; "Reactions of Sodium Borohydride in Acidic Media; XVI. N-Methylation of Amines with Paraformaldehyde/Trifluoroacetic Acid"; *Synthesis*, 1987, pp. 709-711.

Heesen, Michael et al.; "Cloning and chromosomal mapping of an orphan chemokine receptor: mouse RDC1"; 1998, *Immunogenetics*, vol. 47, pp. 364-370.

Kevill, Dennis N. et al.; "Correlation of the Rates of Solvolysis of Allyl and Benzyl Arenesulphonates"; *Journal of Chemical Society Perkin Trans.*, 1984, vol. 2, pp. 717-720.

Kledal, Thomas N. et al.; "A Broad-Spectrum Chemokine Antagonist Encoded by Kaposi's Sarcoma-Associated Herpesvirus"; *Science* 1997, vol. 277, pp. 1656-1659.

Lee, Benhur et al.; "Epitope Mapping of CCR5 Reveals Multiple Conformational States and Distinct but Overlapping Structures Involved in Chemokine and Coreceptor Function"; *The Journal of Biological Chemistry* 1999, vol. 274 No. 14, pp. 9617-9626.

Libert, Frederick et al.; "Selective Amplification and Cloning of Four New Members of the G Protein-Coupled Receptor Family"; 1989, *Science*, vol. 244, No. 4904, pp. 569-572.

Libert, Frederick et al.; "Complete nucleotide sequence of a putative G protein coupled receptor: RDC7"; 1990, *Nucleic Acids Research*, vol. 18, No. 7, pp. 1915.

Lin, Engnian et al.; "Antiangiogenic gene therapy targeting the endothelium-specific receptor tyrosine kinase Tie2"; *Proc. Natl. Acad. Sci.* 1998, vol. 95, pp. 8829-8834.

Liotta, Lance A.; "An attractive force in metastasis"; *Nature*, 2001, vol. 410, pp. 24-25.

Mattson, Ronald J. et al.; "An Improved Method for Reductive Alkylation of Amines Using Titanium (IV) Isopropoxide and Sodium Cyanoborohydride"; *J. Org. Chem.*, 1990, vol. 55, pp. 2552-2554.

Moepps, Barbara et al.; "Two murine homologues of the human chemokine receptor CXCR4 mediating stromal cell-derived factor 1α activation of $G_{i2}$ are differently expressed in vivo"; *Eur. J. Immunol.* 1997, vol. 27, pp. 2102-2112.

Muller, Anja et al.; "Involvement of chemokine receptors in breast cancer metastasis"; *Nature* 2001, vol. 410, pp. 50-56.

Neises, Bernhard et al.; "Simple Method for the Esterification of Carboxylic Acids"; *Angew. Chem. Int. Ed. Engl.*, 1978, vol. 17, No. 7, pp. 522-524.

Neote, Kuldeep, et al.; "Molecular Cloning, Functional Expression, and Signaling Characteristics of a C-C Chemokine Receptor"; *Cell*, 1993, vol. 72, pp. 415-425.

Oppenheim, Joost J. et al.; "Properties of the Novel Proinflammatory Supergene "Intercrine" Cytokine Family"; *Annu. Rev. Immunol.*, 1991, vol. 9, pp. 617-648.

Parolin, Cristina et al.; "Use of Murine CXCR-4 as a Second Receptor by Some T-Cell-Tropic Human Immunodeficiency Viruses"; *Journal of Virology* 1998, vol. 72 No. 2, pp. 1652-1656.

Ponath, Paul D. et al.; "Molecular Cloning and Characterization of a Human Eotaxin Receptor Expressed Selectively on Eosinophils"; *J. Exp. Med.*, 1996, vol. 183, pp. 2437-2448.

Power, Christine A. et al.; "Molecular Cloning and Functional Expression of a Novel CC Chemokine Receptor cDNA from a Human Basophilic Cell Line"; *The Journal of Biological Chemistry*, 1995, vol. 270, No. 33, pp. 19495-19500.

Pulaski, Beth A. et al.; "Cooperativity of *Staphylococcal aureus* Enterotoxin B Superantigen, Major Histocompatibility Complex Class II, and CD80 for Immunotherapy of Advanced Spontaneous Metastases in a Clinically Relevant Postoperative Mouse Breast Cancer Model"; *Cancer Research*, 2000, vol. 60, pp. 2710-2715.

Schall, Thomas J.; "Biology of the Rantes/sis Cytokine Family"; *Cytokine*, 1996, vol. 3, No. 3, pp. 165-183.

Sreedharan, Sunil P. et al.; "Cloning and expression of the human vasoactive intestinal peptide receptor"; 1991, *PNAS*, vol. 88, pp. 4986-4990.

Watanabe, Yoshihisa et al.; "The Selective Amination of Carbonyl Compounds using Iron Pentacarbonyl"; *Tetrahedron Lett.*, 1974, vol. 22, pp. 1879-1880.

Wegner, Scott A. et al.; "Genomic Organization and Functional Characterization of the Chemokine Receptor CXCR4, a Major Entry Co-receptor for Human Immunodeficiency Virus Type 1"; 1998 *The Journal of Biological Chemistry* 1998 vol. 273 No. 8, pp. 4754-4760.

Yoshida, Tetsuya et al.; "Identification of Single C Motif-1/Lymphotactin Receptor XCR1"; *The Journal of Biological Chemistry* 1998, vol. 273 No. 26, pp. 16551-16554.

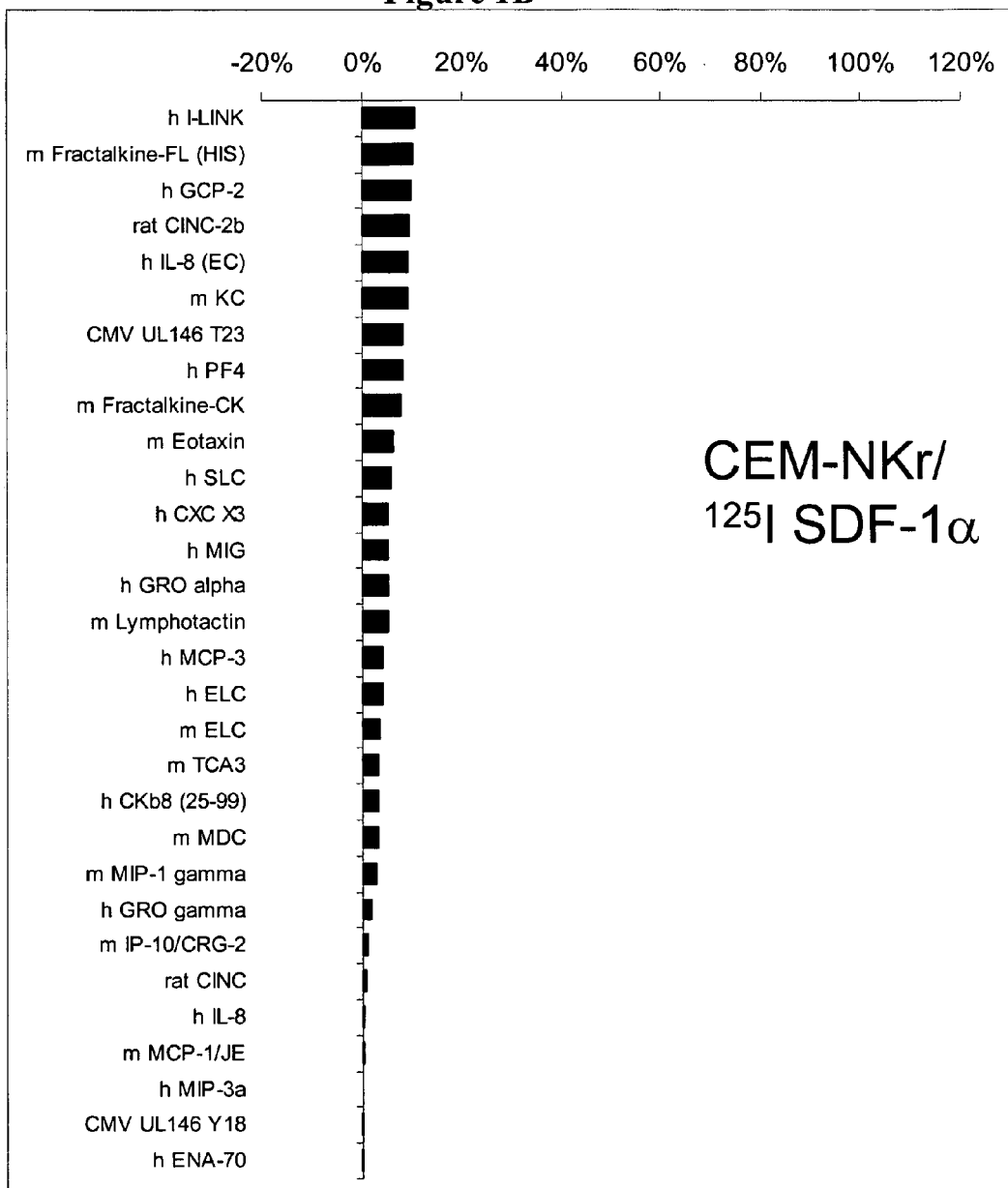

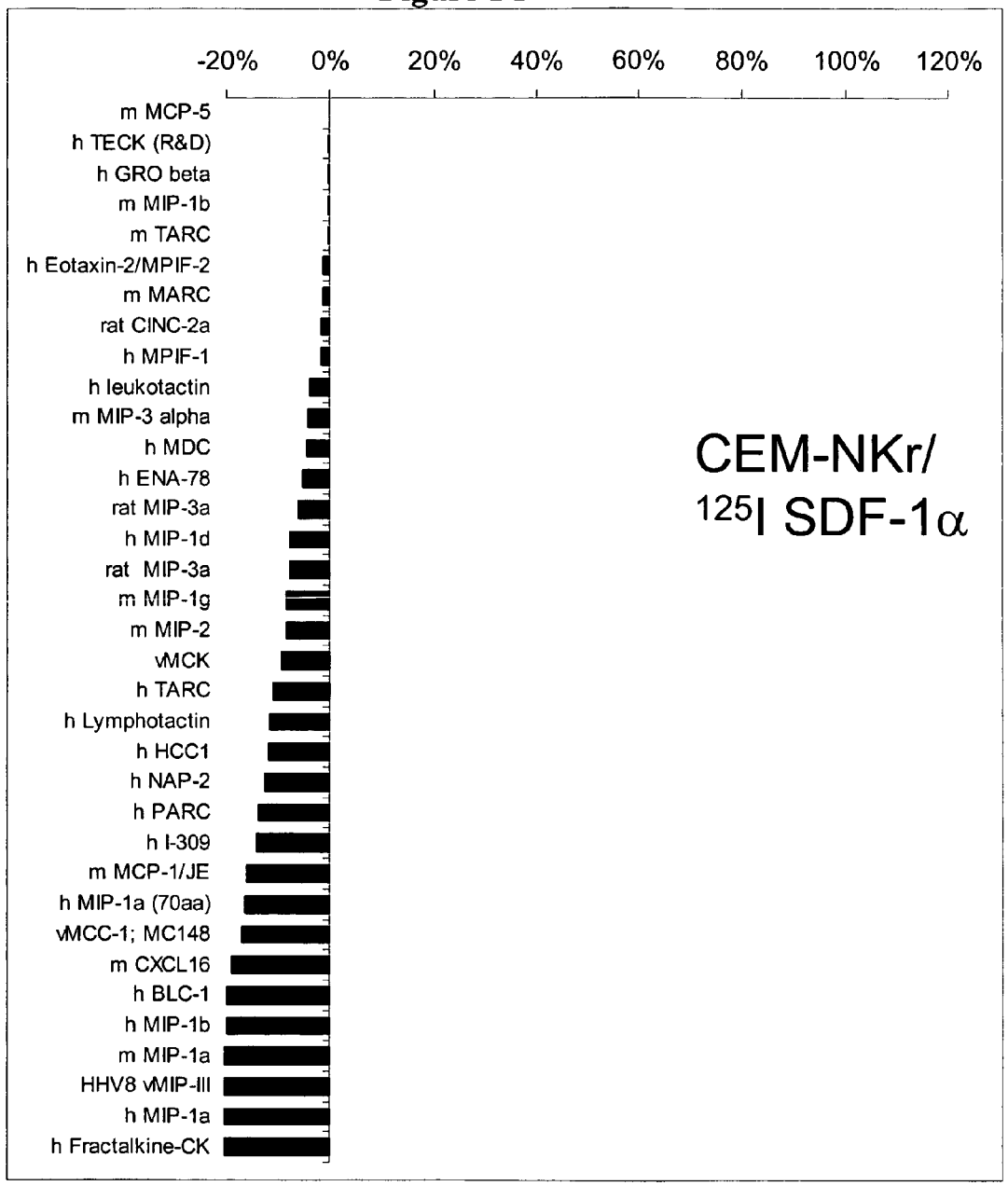

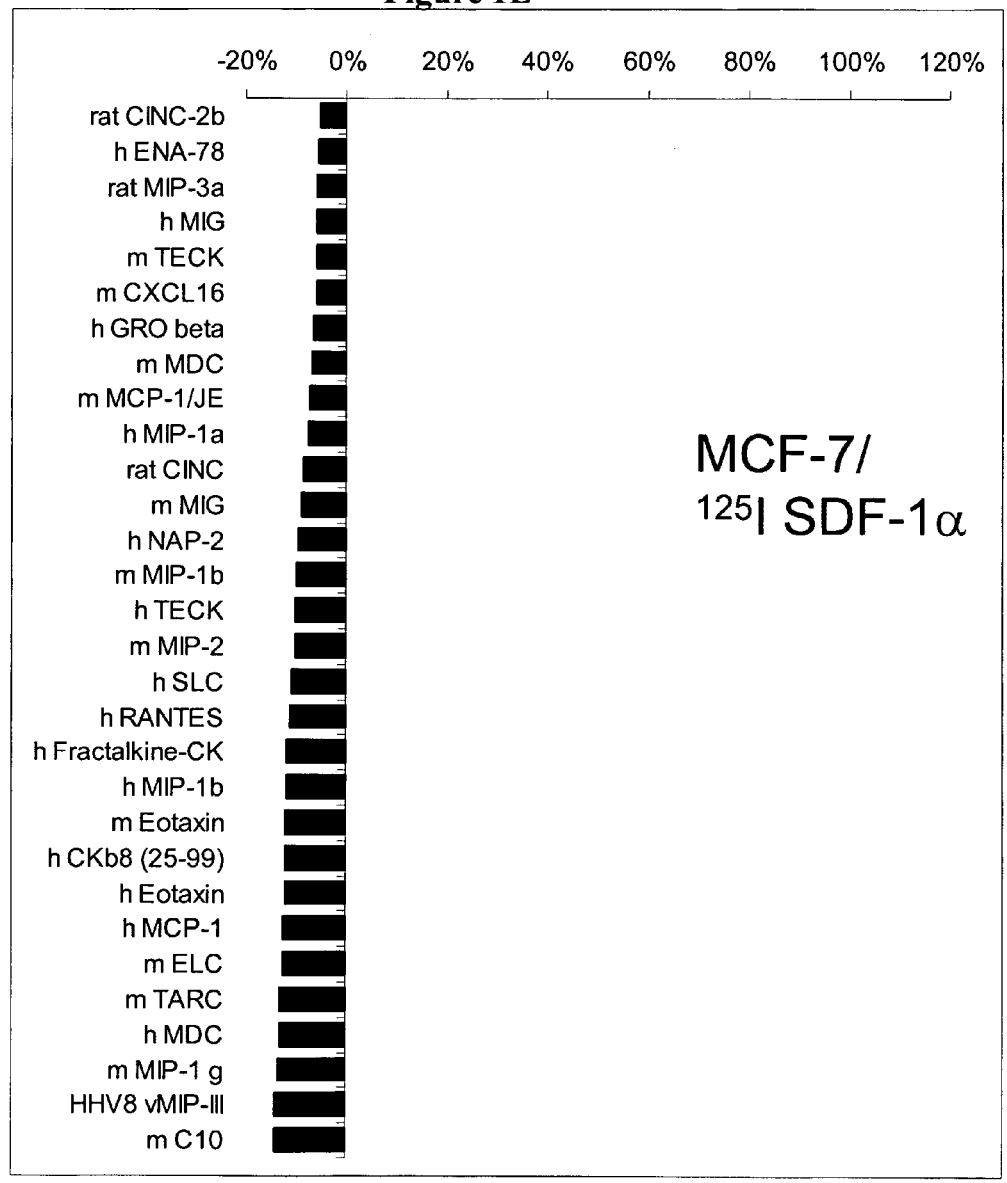

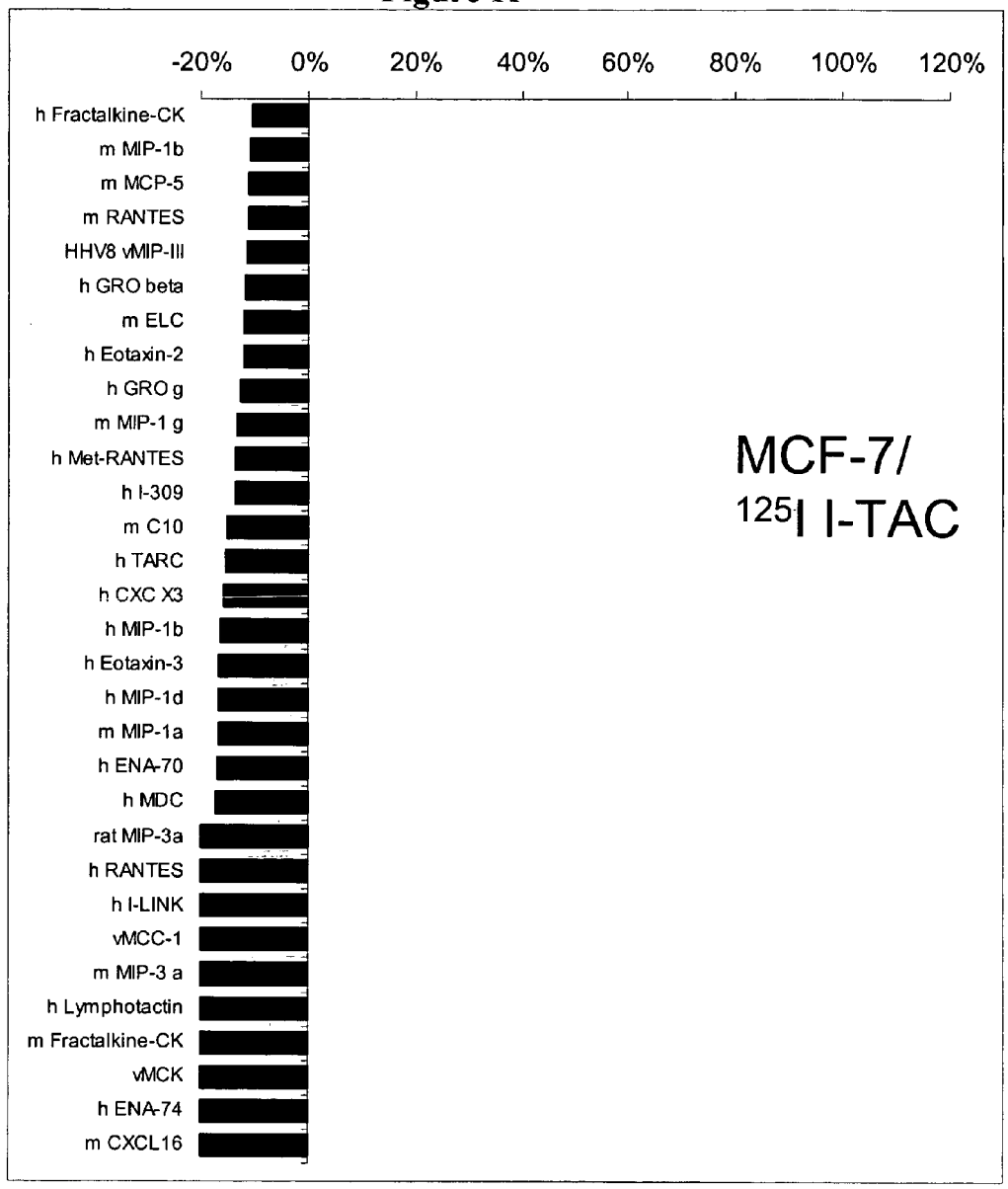

Figure 4
MDA MB 435s CXCR7
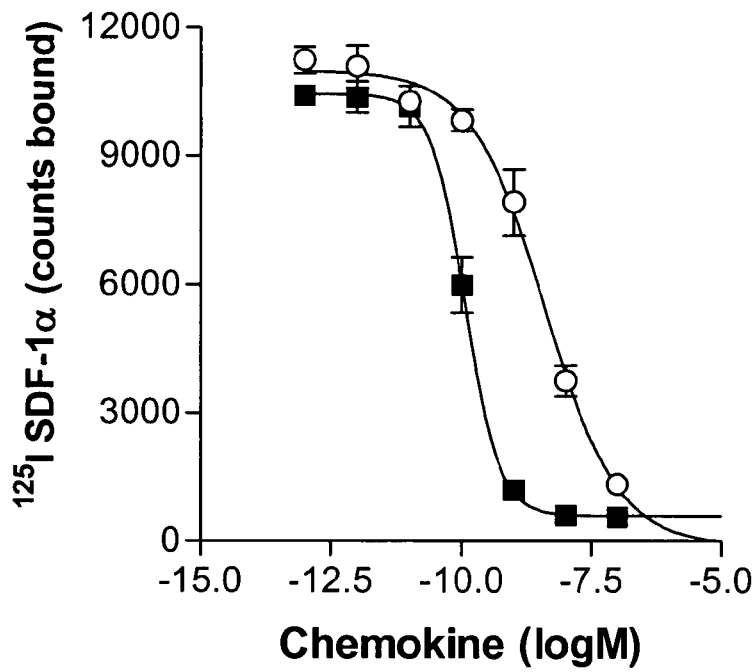
MDA MB 435s wt
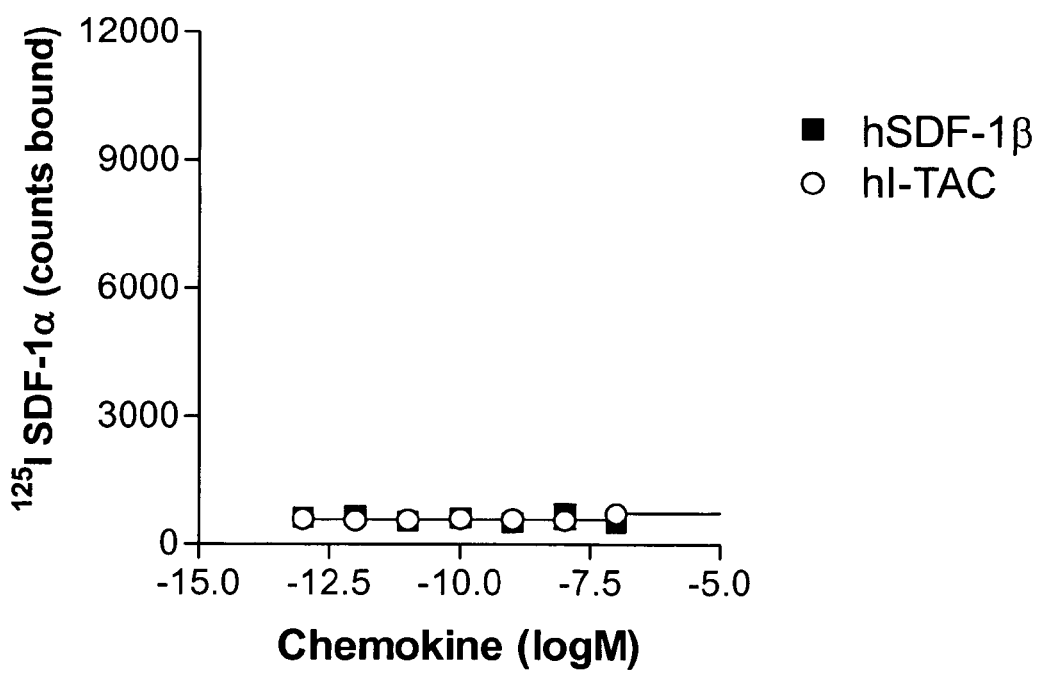
■ hSDF-1β
○ hI-TAC

COMPOSITIONS AND METHODS FOR DETECTING AND TREATING DISEASES AND CONDITIONS RELATED TO CHEMOKINE RECEPTORS

CROSS-REFERENCES TO RELATED APPLICATIONS

The present application is a continuation-in-part of U.S. application Ser. No. 10/698,541, filed Oct. 30, 2003, now U.S. Pat. No. 7,253,007, which is a continuation-in-part of U.S. application Ser. No. 10/452,015, filed May 30, 2003, now U.S. Pat. No. 7,413,866, which is a continuation-in-part of U.S. application Ser. No. 10/245,850, filed Sep. 16, 2002, now U.S. Pat. No. 7,442,512, which claims priority to U.S. Patent Application Ser. No. 60/338,100, filed Nov. 30, 2001 and U.S. Ser. No. 60/337,961, filed Nov. 30, 2001, each of which are explicitly incorporated herein by reference in their entireties and for all purposes. The present application also claims benefit of priority to U.S. Provisional Patent Application No. 60/434,912, filed Dec. 20, 2002, which is explicitly incorporated herein by reference in its entirety and for all purposes.

BACKGROUND OF THE INVENTION

Chemokines constitute a family of small cytokines that are produced in inflammation and regulate leukocyte recruitment, activation and proliferation (Baggiolini, M. et al., *Adv. Immunol.* 55: 97-179 (1994); Springer, T. A., *Annu. Rev. Physiol.* 57: 827-872 (1995); and Schall, T. J. and K. B. Bacon, *Curr. Opin. Immunol.* 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, including T cells and B cells. In addition to stimulating chemotaxis, other changes can be selectively induced by chemokines in responsive cells, including changes in cell shape, transient rises in the concentration of intracellular free calcium ions ($Ca^{2+}$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

Two subfamilies of chemokines, designated as CXC and CC chemokines, are distinguished by the arrangement of the first two of four conserved cysteine residues, which are either separated by one amino acid (as in CXC chemokines SDF-1, IL-8, IP-10, MIG, PF4, ENA-78, GCP-2, GROα, GROβ, GROγ, NAP-2, NAP-4, I-TAC) or are adjacent residues (as in CC chemokines MIP-1α, MIP-1β, RANTES, MCP-1, MCP-2, MCP-3, I-309). Most CXC chemokines attract neutrophil leukocytes. For example, the CXC chemokines interleukin 8 (IL-8), platelet factor 4 (PF4), and neutrophil-activating peptide 2 (NAP-2) are potent chemoattractants and activators of neutrophils. The CXC chemokines designated MIG (monokine induced by gamma interferon) and IP-10 (interferon-γ inducible 10 kDa protein) are particularly active in inducing chemotaxis of activated peripheral blood lymphocytes. CC chemokines are generally less selective and can attract a variety of leukocyte cell types, including monocytes, eosinophils, basophils, T lymphocytes and natural killer cells. CC chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

CC and CXC chemokines act through receptors that belong to a superfamily of seven transmembrane spanning G protein-coupled receptors (Murphy, P. M., *Pharmacol Rev.* 52:145-176 (2000)). This family of G-protein coupled receptors comprises a large group of integral membrane proteins, containing seven transmembrane-spanning regions. The receptors are coupled to G proteins, which are heterotrimeric regulatory proteins capable of binding GTP and mediating signal transduction from coupled receptors, for example, by the production of intracellular mediators.

Generally speaking, chemokine and chemokine receptor interactions tend to be promiscuous in that one chemokine can bind many chemokine receptors and conversely a single chemokine receptor can interact with several chemokines. There are a few exceptions to this rule; one such exception has been the interaction between SDF-1 and CXCR4 (Bleul et al., *J Exp Med*, 184(3): 1101-9 (1996); Oberlin et al., *Nature*, 382(6594): 833-5 (1996)). Originally identified as a pre-B cell growth-stimulating factor (Nagasawa et al., *Proc Natl Acad Sci U S A*, 91(6): 2305-9 (1994)), SDF-1 has been the only reported human ligand for CXCR4. The SDF-1 gene encodes two proteins, designated SDF-1α and SDF-1β, by alternative splicing. These two proteins are identical except for the four amino acid residues that are present in the carboxy-terminus of SDF-1β and absent from SDF-1α.

There are many aspects of chemokine receptor signaling and selectivity for ligands that were not previously understood. For example, there are a number of orphan receptors for which no function has been previously determined. RDC1, for example, though earlier thought to be a receptor for vasoactive intestinal peptide (VIP), is now considered to be an orphan receptor because its endogenous ligand has not been identified. See, e.g., Cook et al., *FEBS Letts.* 300(2): 149-152 (1992).

The present invention addresses these and other issues.

BRIEF SUMMARY OF THE INVENTION

The present invention provides methods of identifying an agent that binds to CCX-CKR2 on a cell. In some embodiments, the method comprises contacting a plurality of agents to a CCX-CKR2 polypeptide comprising an extracellular domain at least 95% identical to an extracellular domain of SEQ ID NO:2, or a SDF1 or I-TAC-binding fragment thereof; and selecting an agent that competes with I-TAC or SDF1 for binding to the CCX-CKR2 polypeptide or fragment thereof, thereby identifying an agent that binds to CCX-CKR2 on a cell.

In some embodiments, the cell is a cancer cell. In some embodiments, the method further comprises testing the selected agent for the ability to bind to, or inhibit growth of, a cell. In some embodiments, the cell is a cancer cell.

In some embodiments, the method further comprises testing the selected agent for the ability to alter kidney function. In some embodiments, the method further comprises testing the selected agent for the ability to alter brain or neuronal function. In some embodiments, the method further comprises testing the selected agent for the ability to change cell adhesion to endothelial cells.

In some embodiments, the agent is less than 1,500 daltons. In some embodiments, the agent is an antibody. In some embodiments, the agent is a polypeptide. In some embodiments, the CCX-CKR2 polypeptide comprises the sequence displayed in SEQ ID NO:2.

The present invention also provides methods for determining the presence or absence of a cancer cell. In some embodiments, the methods comprise contacting a sample comprising a cell with an agent that specifically binds with SEQ ID NO:2; and detecting binding of the agent to a polypeptide in the sample, wherein binding of the agent to the sample indicates the presence of a cancer cell.

In some embodiments, the agent is an antibody. In some embodiments, the agent is less than 1500 daltons. In some embodiments, the agent is a polypeptide. In some embodiments, the polypeptide detected is SEQ ID NO:2. In some embodiments, the sample is from a human. In some embodiments, the method is used to diagnose cancer in a human. In some embodiments, the method is used to provide a prognosis of cancer in a human. In some embodiments, the cancer is selected from the group consisting of cervical cancer, breast cancer, lymphoma, glioblastomas, prostate cancer, and leukemia. In some embodiments, the cancer is not Kaposi's sarcoma, multicentric Castleman's disease or AIDS-associated primary effusion lymphoma. In some embodiments, the antibody competes with SDF1 and I-TAC for binding to SEQ ID NO:2.

The present invention also provides methods of providing a diagnosis or prognosis of an individual having cancer. In some embodiments, the methods comprise detecting the presence or absence of expression of a polynucleotide encoding a CCX-CKR2 polypeptide in a cell of an individual, wherein the CCX-CKR2 polypeptide binds I-TAC and/or SDF1 and the CCX-CKR2 polypeptide is at least 95% identical to SEQ ID NO:2, thereby diagnosing a cancer in the individual.

In some embodiments, the CCX-CKR2 polypeptide is displayed in SEQ ID NO:2. In some embodiments, the cancer is selected from the group consisting of cervical cancer, breast cancer, lymphoma, glioblastomas, prostate cancer, and leukemia. In some embodiments, the cancer is not Kaposi's sarcoma, multicentric Castleman's disease or AIDS-associated primary effusion lymphoma.

The present invention also provides antibodies that specifically competes with SDF-1 and I-TAC for binding to SEQ ID NO:2. In some embodiments, the antibody is a monoclonal antibody. In some embodiments, the antibody is a humanized antibody.

The present invention also provides methods comprising contacting a cell with an agent that specifically binds to SEQ ID NO:2, wherein the agent competes with SDF-1 and I-TAC for binding to a CCX-CKR2 polypeptide, and wherein the cell expresses a CCX-CKR2 polypeptide comprising an extracellular domain at least 95% identical to an extracellular domain of SEQ ID NO:2, thereby binding the agent to the CCX-CKR2 polypeptide on the cell.

In some embodiments, the agent is less than 1,500 daltons. In some embodiments, the agent is an antibody. In some embodiments, the agent is a polypeptide. In some embodiments, the CCX-CKR2 polypeptide is as displayed in SEQ ID NO:2. In some embodiments, the agent is identified by a method comprising contacting a plurality of agents to a CCX-CKR2 polypeptide comprising an extracellular domain at least 95% identical to an extracellular domain of SEQ ID NO:2, or a SDF1 or I-TAC-binding fragment thereof; and selecting an agent that competes with I-TAC or SDF-1 for binding to the CCX-CKR2 polypeptide or fragment thereof, thereby identifying an agent that binds to a cancer cell.

The present invention also provides methods of treating cancer in an individual. In some embodiments, the methods comprise administering to the individual a therapeutically effective amount of a polynucleotide that inhibits expression of a CCX-CKR2 polynucleotide. In some embodiments, the CCX-CKR2 polynucleotide encodes SEQ ID NO:2. In some embodiments, the CCX-CKR2 polynucleotide comprises SEQ ID NO: 1. In some embodiments, the administered polynucleotide inhibits expression via an siRNA.

The present invention also provides methods of treating cancer in an individual. In some embodiments, the methods comprise administering to the individual a therapeutically effective amount of an agent that competes with SDF1 and I-TAC for binding to SEQ ID NO:2. In some embodiments, the agent is less than 1,500 daltons. In some embodiments, the agent is an antibody. In some embodiments, the agent is a polypeptide. In some embodiments, the agent is identified by a method comprising contacting a plurality of agents to a CCX-CKR2 polypeptide comprising an extracellular domain at least 95% identical to an extracellular domain of SEQ ID NO:2, or a SDF1 or I-TAC-binding fragment thereof; and selecting an agent that competes with I-TAC or SDF-1 for binding to the CCX-CKR2 polypeptide or fragment thereof, thereby identifying an agent that binds to a cancer cell. In some embodiments, the cancer is selected from the group consisting of cervical cancer, breast cancer, lymphoma, glioblastomas, prostate cancer, and leukemia. In some embodiments, the cancer is not Kaposi's sarcoma, multicentric Castleman's disease or AIDS-associated primary effusion lymphoma.

BRIEF DESCRIPTION OF THE DRAWINGS

FIGS. 1A-I illustrate binding data demonstrating a distinct SDF-1 displacement binding 'fingerprint' on different cell types. Binding competition profile using $^{125}$I SDF-1α as the radioligand probe on (a) CEM-NKr (FIGS. 1A-C) and (b) MCF-7 (FIGS. 1D-F), as well as $^{125}$I I-TAC (FIGS. 1G-I) used as the radioligand probe on (c) MCF-7, in a binding displacement experiment with a comprehensive array of >90 discrete viral, human and murine chemokines and chemokine variants as cold competitors. The percent inhibition of radioligand binding is shown as a bar graph and reveals that SDF-1α and I-TAC are cross-displaced on MCF-7 but not CEM-NKr cells. White bars, potential high affinity (inhibition>80%); gray bars, potential moderate to low affinity (inhibition between 60-79%); black bars, little or no affinity (inhibition<60%). Results are the mean of three determinations. Error bars are omitted for clarity.

FIG. 4 illustrates that the binding phenotype described herein can be recapitulated in a cell line that does not endogenously express this receptor. The CCX-CKR2 stably transfected breast tumor cell line MDA MB 435s exhibits $^{125}$I SDF-1α binding. This binding can be competed off with cold SDF-1α and I-TAC. By comparison the wildtype cells (not transfected) do not give a productive $^{125}$I SDF-1α binding signal.

DEFINITIONS

Figure 1A:
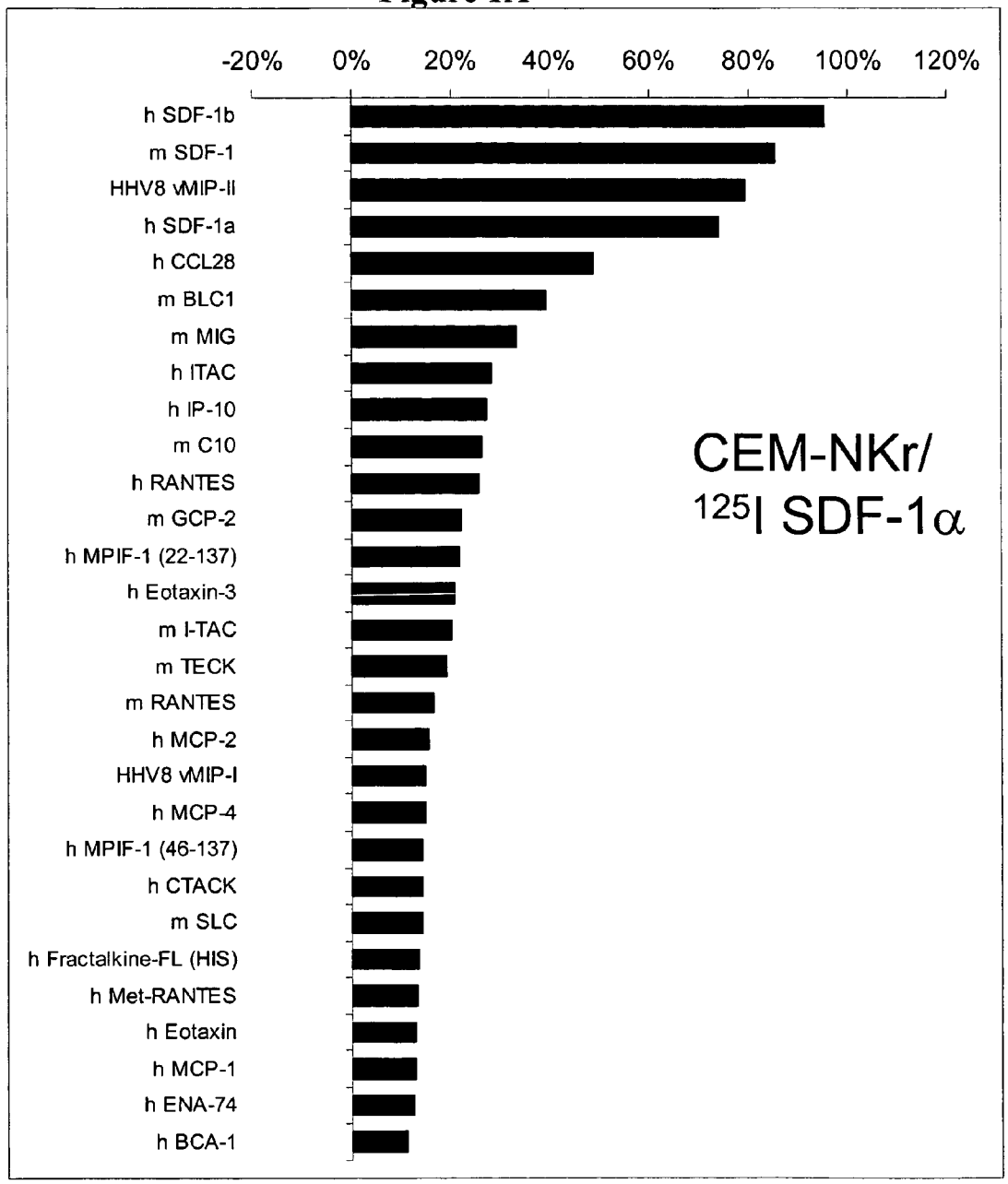
Figure 1D:
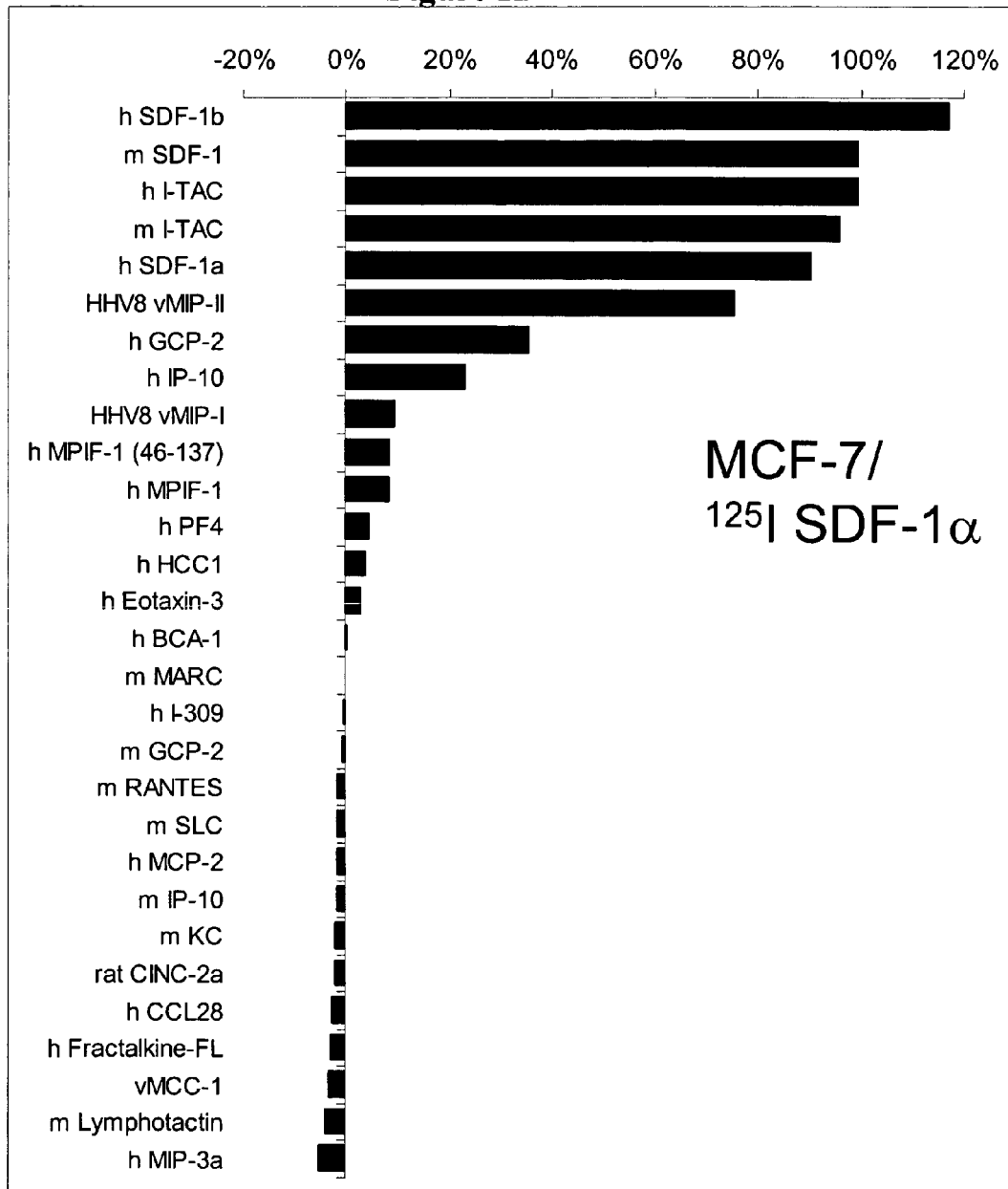
Figure 1F:
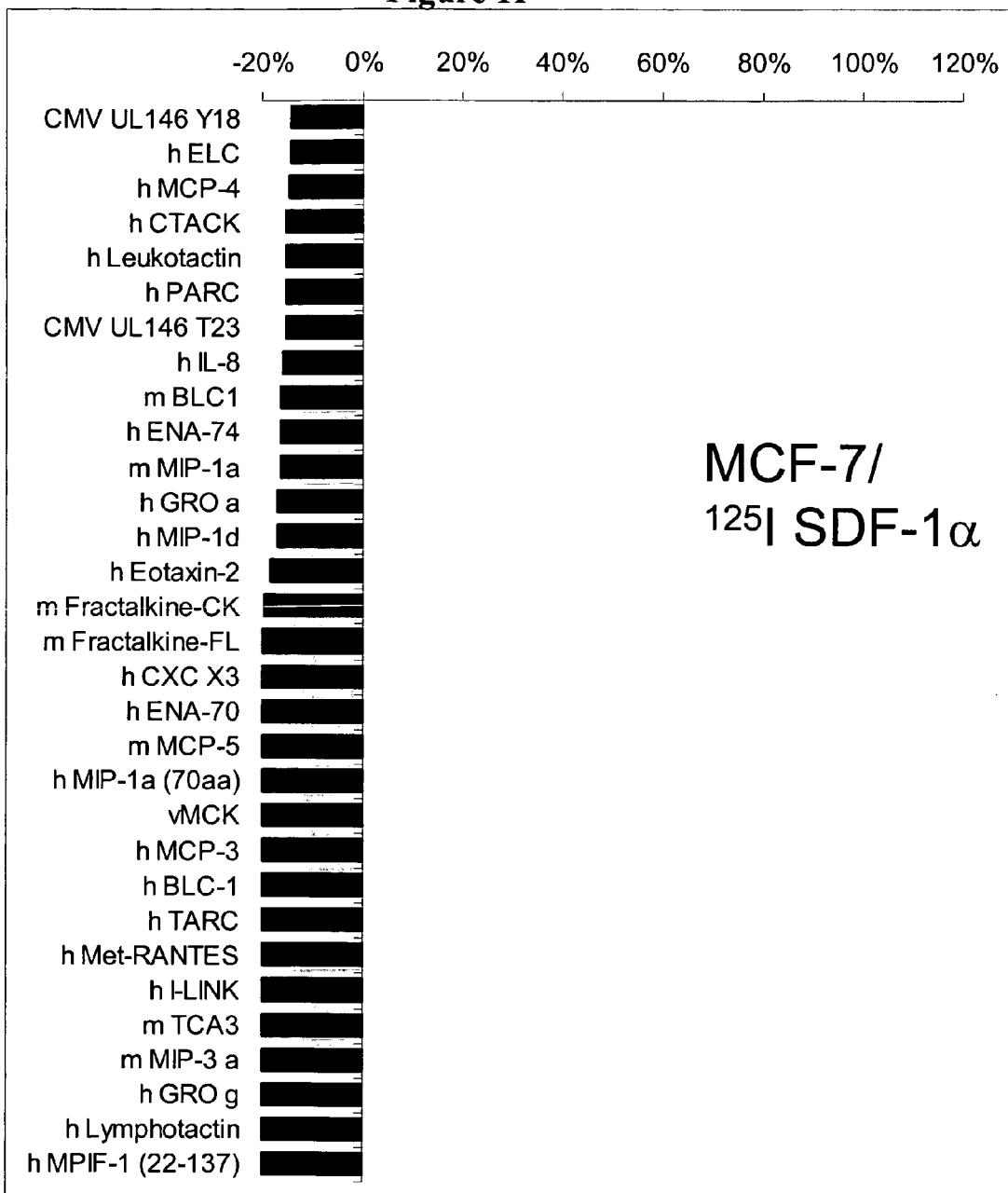
Figure 1G:
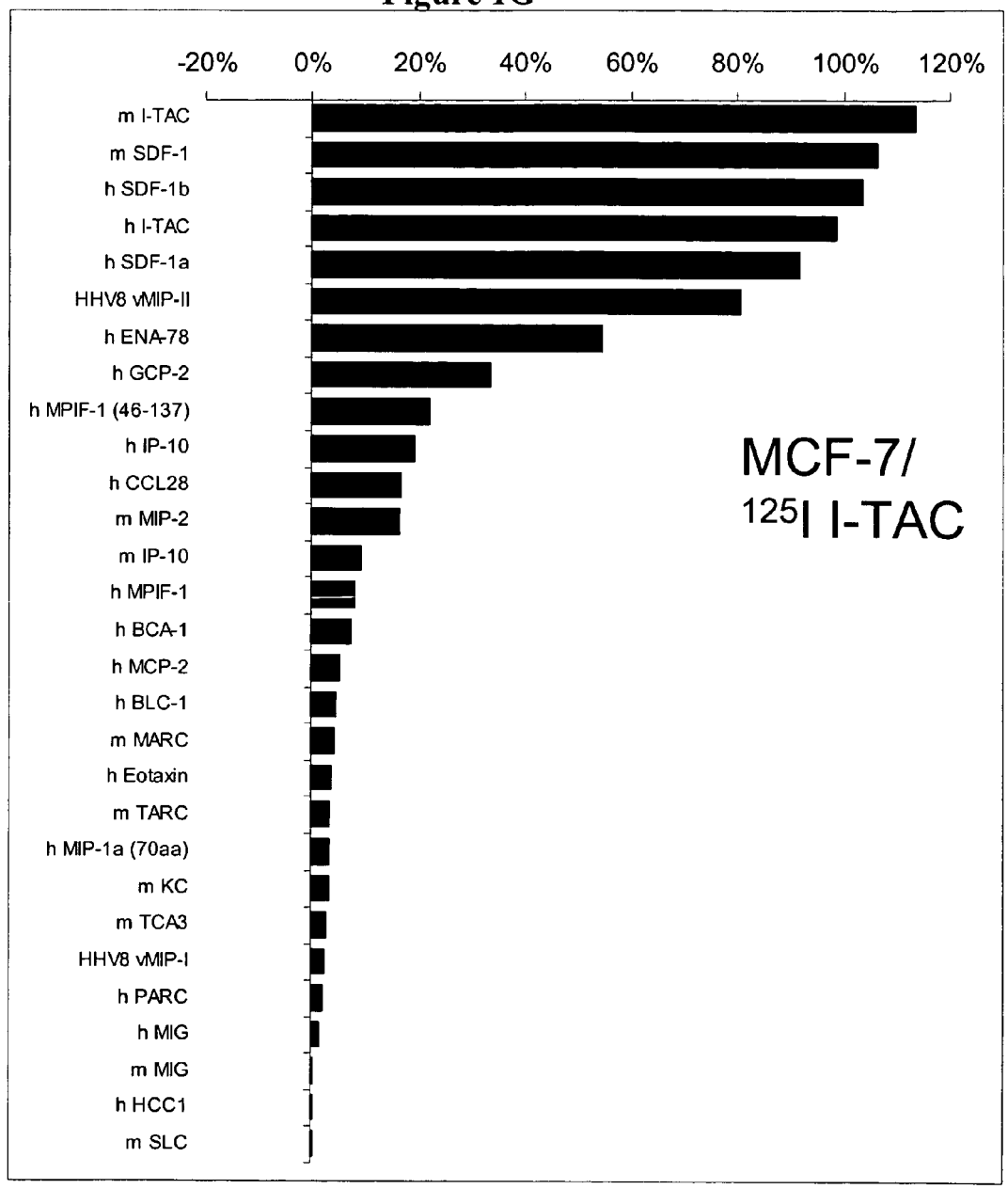
Figure 1H:
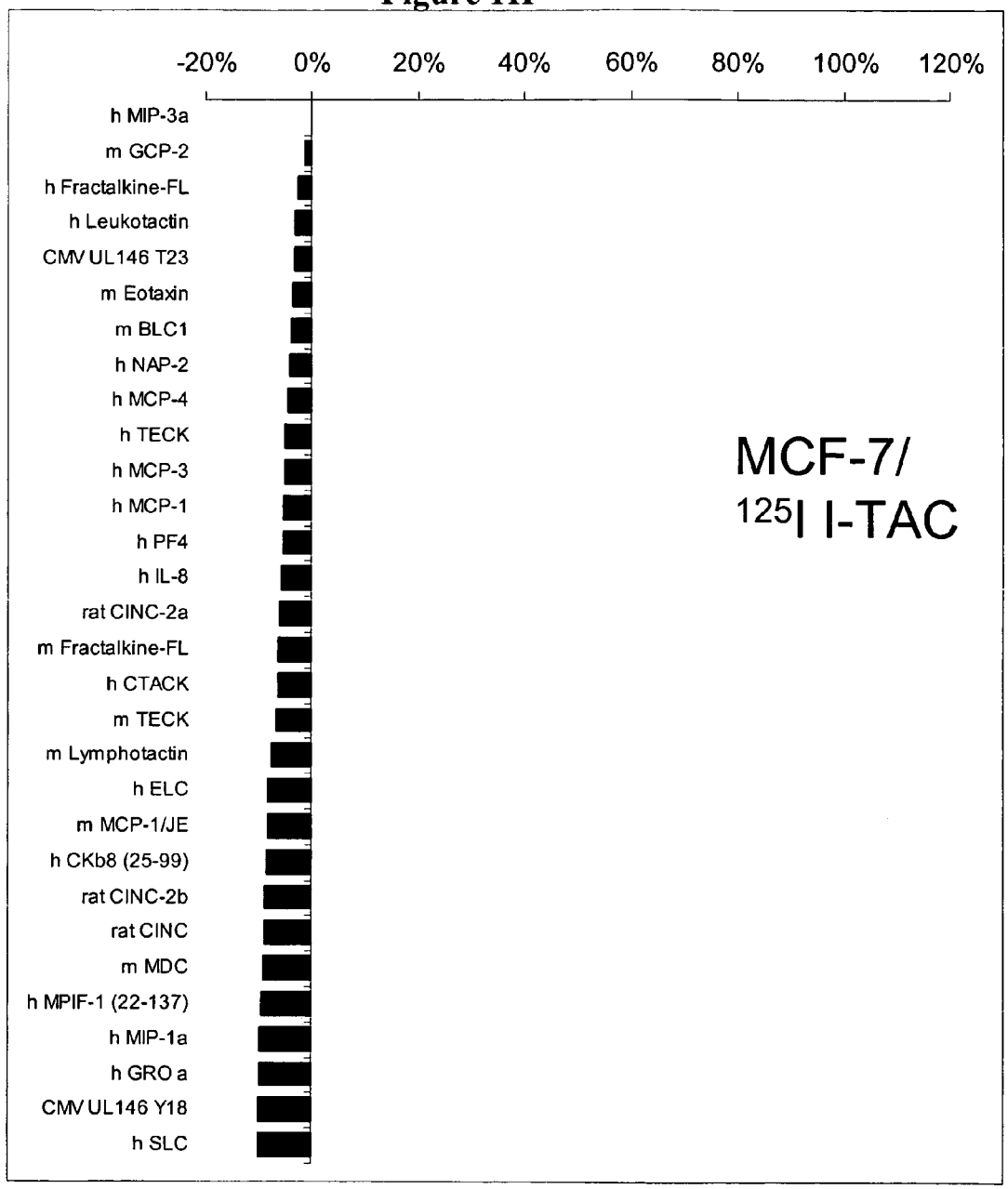

"Chemokine" or "chemokine ligand" refers to a small protein composed of approximately 50 to 110 amino acids and sharing sequence homology with other known chemokines (see, e.g., Murphy, P. M., *Pharmacol Rev.* 52:145-176 (2000)). Chemokines are classified according to the relative positions of the first pair of cysteines (Cs) found in the primary amino acid sequence. In CXCL chemokines, the first pair of cysteines is separated by any single amino acid. CCL chemokines have adjacent cysteines. In the CX3CL chemokines, the first cysteine pair is separated by 3 amino acids. CL chemokines contain only a single cysteine in the homologous position. Chemokines can trigger biological function by binding to and activating chemokine receptors.

A "chemokine receptor" refers to a polypeptide that specifically interacts with a chemokine molecule. A chemokine receptor is typically a G-protein coupled receptor with seven transmembrane domains. Chemokine receptors can possess several common structural features including a highly acidic N-terminal domain; the amino acid sequence DRYLAIVHA (SEQ ID NO:11) (or a minor variation of that sequence) found within the second extracellular loop of many chemokine receptors; a short third intracellular loop with an overall basic charge; a cysteine residue within each of the four extracellular domains. Typically, chemokine receptors have an overall size of approximately 340-370 amino acid residues. See, e.g., reviewed in Murphy, P. M. *Chemokine Receptors; Overview*, Academic Press 2000; and Loetscher P. and Clark-Lewis I. *J. Leukocyte Biol.* 69:881 (2001). Exemplary chemokine receptors include, e.g., CC-chemokine receptors (including CCR1, CCR2, CCR3, CCR4, CCR5, CCR6, CCR7, CCR8, CCR9, and CCR10), CXC-chemokine receptors (including CXCR1, CXCR2, CXCR3, CXCR4, CXCR5, CXCR6 and CCX-CKR2 (e.g., SEQ ID NO:2)), CX3CR1, CXR1, CCXCKR (CCR11), the virally-encoded chemokine receptors, US28, ECRF3, Kaposi's Sarcoma-associated Herpesvirus GPCR (ORF74), Poxvirus membrane-bound G Protein-coupled receptors; D6, and DARC.

Defined responses which may be stimulated by chemokine receptors include transmembrane signaling, activation of cytoplasmic signaling cascades, cytoskeletal rearrangement, adhesion, chemotaxis, invasion, metastasis, cytokine production, gene induction, gene repression, induction of protein expression, or modulation of cellular growth and differentiation, including the development of cancer.

"RDC1," designated herein as "CCX-CKR2" refers to a seven-transmembrane domain presumed G-protein coupled receptor (GPCR). The CCX-CKR2 dog ortholog was originally identified in 1991. See, Libert et al. *Science* 244:569-572 (1989). The dog sequence is described in Libert et al., *Nuc. Acids Res.* 18(7):1917 (1990). The mouse sequence is described in, e.g., Heesen et al., *Immunogenetics* 47:364-370 (1998). The human sequence is described in, e.g., Sreedharan et al., *Proc. Natl. Acad. Sci. USA* 88:4986-4990 (1991), which mistakenly described the protein as a receptor of vasoactive intestinal peptide. "CCX-CKR2" includes sequences that are substantially similar to or conservatively modified variants of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

The terms "peptidomimetic" and "mimetic" refer to a synthetic chemical compound that has substantially the same structural and functional characteristics of antagonists or agonists of a chemokine receptor. Peptide analogs are commonly used in the pharmaceutical industry as non-peptide drugs with properties analogous to those of the template peptide. These types of non-peptide compound are termed "peptide mimetics" or "peptidomimetics" (Fauchere, J. *Adv. Drug Res.* 15:29 (1986); Veber and Freidinger *TINS* p. 392 (1985); and Evans et al. *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of, e.g., —CH2NH—, —CH2S—, —CH2-CH2-, —CH=CH— (cis and trans), —COCH2-, —CH(OH)CH2—, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. A mimetic can, for example, mimic the binding of SDF-1 or I-TAC to CCX-CKR2. For example, a mimetic composition is within the scope of the invention if it is capable of inhibiting or increasing the activity or function of CCX-CKR2.

"Antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to V$_H$—C$_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv).

"Humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants, e.g., proteins at least 80%, 85%, 90%, 95% or 99% identical to SEQ ID NO:2. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

A "ligand" refers to an agent, e.g., a polypeptide or other molecule, capable of binding to a chemokine receptor.

As used herein, "an agent that binds to a chemokine receptor" refers to an agent that binds to the chemokine receptor with a high affinity. "High affinity" refers to an affinity sufficient to induce a pharmacologically relevant response, e.g., the ability to significantly compete for binding with a natural chemokine ligand to a chemokine receptor at pharmaceutically relevant concentrations (e.g., at concentrations lower than about $10^{-5}$ M.) See, e.g., Example 1 and FIG. 5. Some exemplary agents with high affinity will bind to a chemokine receptor with an affinity greater than $10^{-6}$ M, and sometimes greater than $10^{-7}$ M, or $10^{-8}$ M. An agent that fails to compete for binding with a natural receptor ligand when the agent is in a concentrations lower than $10^{-4}$ M will be considered to "not bind" for the purposes of the invention.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants"

refers to those nucleic acids that encode identical or essentially identical amino acid sequences, or where the nucleic acid does not encode an amino acid sequence, to essentially identical sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region, e.g., of the entire polypeptide sequences of the invention or the extra-cellular domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region or the entire sequence of a polynucleotide, e.g., of the entire polypeptide sequences of the invention such as CCX-CKR2 (e.g., SEQ ID NO:2) or the extra-cellular domains of the polypeptides of the invention, when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Modulators" of CCX-CKR2 activity are used to refer to molecules that increase or decrease CCX-CKR2 activity directly or indirectly and includes those molecules identified using in vitro and in vivo assays for CCX-CKR2 binding or signaling. CCX-CKR2 activity can be increased, e.g., by contacting the CCX-CKR2 polypeptide with an agonist, and/or, in some cases, by expressing CCX-CKR2 in a cell. Agonists refer to molecules that increase activity of CCX-CKR2. Agonists are agents that, e.g., bind to, stimulate, increase, open, activate, facilitate, enhance activation, sensitize or up regulate the activity of CCX-CKR2. Modulators may compete for binding to CCX-CKR2 with known CCX-CKR2 ligands such as SDF-1 and I-TAC and small molecules as described herein.

Antagonists refer to molecules that inhibit CCX-CKR2 activity, e.g., by blocking binding of agonists such as I-TAC or SDF-1. Antagonists are agents that, e.g., bind to, partially or totally block stimulation, decrease, prevent, delay activation, inactivate, desensitize, or down regulate the activity of CCX-CKR2.

Modulators include agents that, e.g., alter the interaction of CCX-CKR2 with: proteins that bind activators or inhibitors, receptors, including G-proteins coupled-receptors (GPCRs), kinases, etc. Modulators include genetically modified versions of naturally-occurring chemokine receptor ligands, e.g., with altered activity, as well as naturally occurring and synthetic ligands, antagonists, agonists, small chemical molecules, siRNAs and the like. Assays for inhibitors and activators include, e.g., applying putative modulator compounds to a cell expressing CCX-CKR2 and then determining the functional effects on CCX-CKR2 signaling, e.g., ERK1 and/or ERK2 phosphorylation or activation of members of the ERK1 or ERK2 signal transduction pathway, and/or other effects as described herein. Samples or assays comprising CCX-CKR2 that are treated with a potential activator, inhibitor, or modulator are compared to control samples without the inhibitor, activator, or modulator to examine the extent of inhibition. Control samples (untreated with inhibitors) are assigned a relative chemokine receptor activity value of 100%. Inhibition of CCX-CKR2 is achieved when CCX-CKR2 activity or expression value relative to the control is less than about 95%, optionally about 90%, optionally about 80%, optionally about 50% or about 25-0%. Activation of CCX-CKR2 is achieved when CCX-CKR2 activity or expression value relative to the control is at least about 105%, about 110%, optionally at least about 105%, about 150%, optionally at least about 105%, about 200-500%, or at least about 105%, about 1000-3000% or higher.

"siRNA" refers to small interfering RNAs, that are capable of causing interference with gene expression and can cause post-transcriptional silencing of specific genes in cells, for example, mammalian cells (including human cells) and in the body, for example, mammalian bodies (including humans). The phenomenon of RNA interference is described and discussed in Bass, Nature 411: 428-29 (2001); Elbahir et al., Nature 411: 494-98 (2001); and Fire et al., Nature 391: 806-11 (1998); and WO 01/75164, where methods of making interfering RNA also are discussed. The siRNAs based upon the sequences and nucleic acids encoding the gene products disclosed herein typically have fewer than 100 base pairs and can be, e.g., about 30 bps or shorter, and can be made by approaches known in the art, including the use of complementary DNA strands or synthetic approaches. The siRNAs are capable of causing interference and can cause post-transcriptional silencing of specific genes in cells, for example, mammalian cells (including human cells) and in the body, for example, mammalian bodies (including humans). Exemplary siRNAs according to the invention could have up to 29 bps, 25 bps, 22 bps, 21 bps, 20 bps, 15 bps, 10 bps, 5 bps or any integer thereabout or therebetween. Tools for designing optimal inhibitory siRNAs include that available from DNAengine Inc. (Seattle, Wash.) and Ambion, Inc. (Austin, Tex.).

One RNAi technique employs genetic constructs within which sense and anti-sense sequences are placed in regions flanking an intron sequence in proper splicing orientation with donor and acceptor splicing sites. Alternatively, spacer sequences of various lengths may be employed to separate self-complementary regions of sequence in the construct.

During processing of the gene construct transcript, intron sequences are spliced-out, allowing sense and anti-sense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes.

The term "compound" refers to a specific molecule and includes its enantiomers, diastereomers, polymorphs and salts thereof.

The term "heteroatom" refers to a bonded nitrogen, oxygen, or sulfur atom.

The term "substituted" refers to a group that is bonded to a parent molecule or group. Thus, a benzene ring having a methyl substituent is a methyl-substituted benzene. Similarly, a benzene ring having 5 hydrogen substituents would be an unsubstituted phenyl group when bonded to a parent molecule.

The term "substituted heteroatom" refers to a group where a heteroatom is substituted. The heteroatom may be substituted with a group or atom, including, but not limited to hydrogen, halogen, alkyl, alkylene, alkenyl, alkynyl, aryl, arylene, cycloalkyl, cycloalkylene, heteroaryl, heteroarylene, heterocyclyl, carbocycle, hydroxy, alkoxy, aryloxy, and sulfonyl. Representative substituted heteroatoms include, by way of example, cyclopropyl aminyl, isopropyl aminyl, benzyl aminyl, and phenoxy.

The term "alkyl" refers to a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl, and the like.

The term "alkylene" refers to a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl, and the like.

The term "alkenyl" refers to a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl, and the like.

The term "alkynyl" refers to a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl, and the like.

The term "aryl" refers to a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "arylene" refers to a divalent aromatic hydrocarbon having a single ring (i.e., phenylene) or fused rings (i.e., naphthalenediyl). Unless otherwise defined, such arylene groups typically contain from 6 to 10 carbon ring atoms. Representative arylene groups include, by way of example, 1,2-phenylene, 1,3-phenylene, 1,4-phenylene, naphthalene-1,5-diyl, naphthalene-2,7-diyl, and the like.

The term "aralkyl" refers to an aryl substituted alkyl group. Representative aralkyl groups include benzyl.

The term "cycloalkyl" refers to a monovalent saturated carbocyclic hydrocarbon group having a single ring or fused rings. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl, and the like.

The term "cycloalkylene" refers to a divalent saturated carbocyclic hydrocarbon group having a single ring or fused rings. Unless otherwise defined, such cycloalkylene groups typically contain from 3 to 10 carbon atoms. Representative cycloalkylene groups include, by way of example, cyclopropane-1,2-diyl, cyclobutyl-1,2-diyl, cyclobutyl-1,3-diyl, cyclopentyl-1,2-diyl, cyclopentyl-1,3-diyl, cyclohexyl-1,2-diyl, cyclohexyl-1,3-diyl, cyclohexyl-1,4-diyl, and the like.

The term "heteroaryl" refers to a substituted or unsubstituted monovalent aromatic group having a single ring or fused rings and containing in the ring at least one heteroatom (typically 1 to 3 heteroatoms) selected from nitrogen, oxygen, or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heteroarylene" refers to a divalent aromatic group having a single ring or fused rings and containing at least one heteroatom (typically 1 to 3 heteroatoms) selected from nitrogen, oxygen or sulfur in the ring. Unless otherwise defined, such heteroarylene groups typically contain from 5 to 10 total ring atoms. Representative heteroarylene groups include, by way of example, divalent species of pyrrole, imidazole, thiazole, oxazole, furan thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The terms "heterocyclyl" or "heterocyclic group" refer to a substituted or unsubstituted monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring atoms. Representative heterocyclic groups include, by way of example, monovalent species of pyrrolidine, morpholine, imidazolidine, pyrazolidine, piperidine, 1,4-dioxane, thiomorpholine, piperazine, 3-pyrroline and the like, where the point of attachment is at any available carbon or nitrogen ring atom.

The term "carbocycle" refers to an aromatic or non-aromatic ring in which each atom in the ring is carbon. Representative carbocycles include cyclohexane, cyclohexene, and benzene.

The terms "halo" or "halogen" refers to fluoro-(—F), chloro-(—Cl), bromo-(—Br), and iodo-(—I).

The term "hydroxy" or "hydroxyl" refers to an —OH group.

The term "alkoxy" refers to an —OR group, where R can be a substituted or unsubstituted alkyl, alkylene, cycloalkyl, or cycloalkylene. Suitable substituents include halo, cyano, alkyl, amino, hydroxy, alkoxy, and amido. Representative alkoxy groups include, by way of example, methoxy, ethoxy, isopropyloxy, and trifluoromethoxy.

The term "aryloxy" refers to an —OR group, where R can be a substituted or unsubstituted aryl or heteroaryl group. Representative aryloxy groups include phenoxy.

The term "sulfonyl" refers to a —S(O)2- or —S(O)2R group, where R can be alkyl, alkylene, alkenyl, alkynyl, aryl, cycloalkyl, cycloalkylene, heteroaryl, heteroarylene, heterocyclic, or halogen. Representative sulfonyl groups include, by way of example, sulfonate, sulfonamide, sulfonyl halides, and dipropylamide sulfonate.

The term "condensation" refers to a reaction in which two or more molecules are covalently joined. Likewise, condensation products are the products formed by the condensation reaction.

DETAILED DESCRIPTION OF THE INVENTION

I. Introduction

The present invention provides the discovery that the orphan receptor RDC1, referred to herein as CCX-CKR2, binds the chemokine ligands SDF1 and I-TAC. Moreover, the present invention provides the surprising discovery of CCX-CKR2's involvement in cancer. Thus, the invention provides methods of diagnosing cancer by detecting CCX-CKR2. The invention also provides methods of inhibiting cancer by administering a modulator of CCX-CKR2 to an individual with cancer.

II. CCX-CKR2 Polypeptides and Polynucleotides

In numerous embodiments of the present invention, nucleic acids encoding CCX-CKR2 polypeptides of interest will be isolated and cloned using recombinant methods. Such embodiments are used, e.g., to isolate CCX-CKR2 polynucleotides (e.g., SEQ ID NO:1, SEQ ID NO:3, SEQ ID NO:5, SEQ ID NO:7, and SEQ ID NO:9)) for protein expression or during the generation of variants, derivatives, expression cassettes, or other sequences derived from a CCX-CKR2 polypeptide (e.g., SEQ ID NO:2, SEQ ID NO:4, SEQ ID NO:6, SEQ ID NO:8, and SEQ ID NO:10)), to monitor CCX-CKR2 gene expression, for the isolation or detection of CCX-CKR2 sequences in different species, for diagnostic purposes in a patient, e.g., to detect mutations in CCX-CKR2 or to detect expression of CCX-CKR2 nucleic acids or CCX-CKR2 polypeptides. In some embodiments, the sequences encoding CCX-CKR2 are operably linked to a heterologous promoter. In some embodiments, the nucleic acids of the invention are from any mammal, including, in particular, e.g., a human, a mouse, a rat, a dog, etc.

In some cases, the CCX-CKR2 polypeptides of the invention comprise the extracellular amino acids of the human CCX-CKR2 sequence (e.g., of SEQ ID NO:2, SEQ ID NO:4, SEQ ID NO:6, SEQ ID NO:8, and SEQ ID NO:10)) while other residues are either altered or absent. In other embodiments, the CCX-CKR2 polypeptides comprise ligand-binding fragments of CCX-CKR2. For example, in some cases, the fragments bind I-TAC and/or SDF1. The structure of seven trans-membrane receptors (of which CCX-CKR2 is one) are well known to those skilled in the art and therefore trans-membrane domains can be readily determined. For example, readily available hydrophobicity algorithms can be found on the internet at the G Protein-Coupled Receptor Data Base (GPCRDB), e.g., world wide web at gpcr.org/7tm/seq/ DR/RDC1_HUMAN.TABDR.html or world wide web at gpcr.org/7tm/seq/vis/swac/P25106.html.

This invention relies on routine techniques in the field of recombinant genetics. Basic texts disclosing the general methods of use in this invention include Sambrook et al., *Molecular Cloning, A Laboratory Manual* (3rd ed. 2001); Kriegler, Gene *Transfer and Expression: A Laboratory Manual* (1990); and *Current Protocols in Molecular Biology* (Ausubel et al., eds., 1994)).

Appropriate primers and probes for identifying the genes encoding CCX-CKR2 from mammalian tissues can be derived from the sequences provided herein (e.g., SEQ ID NO: 1). For a general overview of PCR, see, Innis et al. *PCR Protocols: A Guide to Methods and Applications*, Academic Press, San Diego (1990).

III. Development of Specific Therapeutics

Molecules that bind to CCX-CKR2, including modulators of CCX-CKR2 function, i.e. agonists or antagonists or agents of CCX-CKR2 activity, are useful for treating a number of mammalian diseases, including cancer.

Diseases or conditions of humans or other species which can be treated with antagonists of a chemokine receptor or other inhibitors of chemokine receptor function, include, but are not limited to, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers); as well as brain and neuronal dysfunction, such as Alzheimer's disease and multiple sclerosis; kidney dysfunction; rheumatoid arthritis; cardiac allograft rejection; atherosclerosis; asthma; glomerulonephritis; contact dermatitis; inflammatory bowel disease; colitis; psoriasis; reperfusion injury; as well as other disorders and diseases described herein.

Alternatively, an agonist of CCX-CKR2 can be used to treat disease, e.g., in renal, brain or neuronal dysfunction as well as in cases where stem cell mobilization is therapeutic.

A. Methods of Identifying Modulators of Chemokine Receptors

A number of different screening protocols can be utilized to identify agents that modulate the level of activity or function of CCX-CKR2 in cells, particularly in mammalian cells, and especially in human cells. In general terms, the screening methods involve screening a plurality of agents to identify an agent that interacts with CCX-CKR2 (or an extracellular domain thereof), for example, by binding to CCX-CKR2, preventing a ligand (e.g., I-TAC and/or SDF1) from binding to CCX-CKR2 or activating CCX-CKR2. In some embodiments, an agent binds CCX-CKR2 with at least about 1.5, 2, 3, 4, 5, 10, 20, 50, 100, 300, 500, or 1000 times the affinity of the agent for another protein.

1. Chemokine Receptor Binding Assays

In some embodiments, CCX-CKR2 modulators are identified by screening for molecules that compete with a ligand of CCX-CKR2 such as SDF1 or I-TAC. Those of skill in the art will recognize that there are a number of ways to perform competition analyses. In some embodiments, samples with CCX-CKR2 are pre-incubated with a labeled CCX-CKR2 ligand and then contacted with a potential competitor molecule. Alteration (e.g., a decrease) of the quantity of ligand bound to CCX-CKR2 indicates that the molecule is a potential CCX-CKR2 modulator.

Preliminary screens can be conducted by screening for agents capable of binding to a CCX-CKR2, as at least some of the agents so identified are likely chemokine receptor modulators. The binding assays usually involve contacting CCX-CKR2 with one or more test agents and allowing sufficient time for the protein and test agents to form a binding complex. Any binding complexes formed can be detected using any of a number of established analytical techniques. Protein binding assays include, but are not limited to, immunohistochemical binding assays, flow cytometry, radioligand binding, europium labeled ligand binding, biotin labeled ligand binding or other assays which maintain the conformation of CCX-CKR2. The chemokine receptor utilized in such assays can be naturally expressed, cloned or synthesized. For example, by contacting CCX-CKR2 with a potential agonist and measuring for CCX-CKR2 activity, it is possible to identify those molecules that stimulate CCX-CKR2 activity.

2. Cells and Reagents

The screening methods of the invention can be performed as in vitro or cell-based assays. In vitro assays are performed for example, using membrane fractions or whole cells comprising CCX-CKR2. Cell based assays can be performed in any cells in which CCX-CKR2 is expressed.

Cell-based assays involve whole cells or cell fractions containing CCX-CKR2 to screen for agent binding or modulation of activity of CCX-CKR2 by the agent. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells, endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, CCX-CKR2 can be expressed in cells that do not express an endogenous version of CCX-CKR2.

In some cases, fragments of CCX-CKR2, as well as protein fusions, can be used for screening. When molecules that compete for binding with CCX-CKR2 ligands are desired, the CCX-CKR2 fragments used are fragments capable of binding the ligands (e.g., capable of binding I-TAC or SDF1). Alternatively, any fragment of CCX-CKR2 can be used as a target to identify molecules that bind CCX-CKR2. CCX-CKR2 fragments can include any fragment of, e.g., at least 20, 30, 40, 50 amino acids up to a protein containing all but one amino acid of CCX-CKR2. Typically, ligand-binding fragments will comprise transmembrane regions and/or most or all of the extracellular domains of CCX-CKR2.

3. Signaling Activity

In some embodiments, signaling triggered by CCX-CKR2 activation is used to identify CCX-CKR2 modulators. Signaling activity of chemokine receptors can be determined in many ways. For example, signaling can be determined by detecting chemokine receptor-mediated cell adhesion. Interactions between chemokines and chemokine receptors can lead to rapid adhesion through the modification of integrin affinity and avidity. See, e.g., Laudanna, *Immunological Reviews* 186:37-46 (2002).

Signaling can also be measured by determining, qualitatively and quantitatively, secondary messengers, such as cyclic AMP or inositol phosphates, as well as phosphorylation or dephosphorylation events can also be monitored. See, e.g., Premack, et al. *Nature Medicine* 2: 1174-1178 (1996) and Bokoch, *Blood* 86:1649-1660 (1995).

The examples provide results demonstrating that CCX-CKR2 activity is mediated by the MAPK pathway, specifically that CCX-CKR2 promotes the phosphorylation of the MAPK proteins ERK1 and ERK2. An exemplary native sequence ERK1 is provided in GenBank Accession No. p27361; an exemplary native sequence ERK2 is provided in GenBank Accession No. p28482. Thus, some assays are designed to detect a signal in the MAPK pathway. The term "signal" as used with respect to the MAPK pathway refers to a component that is part of the pathway and/or some activity or manifestation associated with the pathway. The component can be any molecule (e.g., a protein) involved (e.g., produced, utilized or modified) in the MAPK signal transduction pathway. The signal in some instances is detection of the phosphorylation of a MAPK protein such as ERK1 or ERK2. Other signals that can be detected include the components that are formed and/or utilized downstream of the phosphorylation of ERK1 or ERK2, as well as activities associated with the formation and utilization of these components. Some assays can be conducted to detect components that are formed and/or utilized upstream of the phosphorylation of ERK1 or ERK2, as well as activities associated with the production or utilization of such upstream components. As indicated above, In the case of ERK1 or ERK2, upstream components include, for example, Ras, a MKKK (e.g., c-Raf1, B-Raf, and A-Raf), and a MKK (e.g., MKK1 and MKK2). Downstream components include, for example, the protein p90RSK, c-JUN, c-FOS, CREB and STAT. Thus, each of these components can be detected in certain assays and/or the modification (e.g., phosphorylation) of these components. In addition, gene expression profiling and protein secretion could also be detected.

Some of the screening assays that are provided involve detecting the phosphorylation of ERK1 and/or ERK2. Phosphorylation of these proteins is ligand (e.g., SDF1, ITAC) dependent. Thus, the assays in certain screening methods are conducted in the presence of ITAC or SDF1 to promote the phosphorylation of ERK1 and ERK2. When assays are conducted with ITAC and SDF1, the assay can be simplified using cells that do not express CXCR3 or CXCR4 for the reasons described above.

Determining whether ERK1 or ERK2 has been phosphorylated can be performed using various approaches. One option is to lyse the cells after they have been incubated with a CCX-CKR2 ligand and a test agent. The resulting lysate can then be analyzed by Western blot by electrophoresing the lysate to separate proteins on a gel and then probing the gel with antibodies that specifically bind to the phosphorylated form of ERK1 or ERK2. Such antibodies are available from Cell Signaling Technologies of Beverly, Mass. The total amount of ERK1 or ERK2 present can optionally be determined using antibodies that specifically bind both the phosphorylated and unphosphorylated forms of ERK1 and ERK2. Further details regarding this approach are set forth in the examples. Another option that is suited for high throughput screening is to use an ELISA method using antibodies that specifically bind the phosphorylated forms of ERK1 and ERK2. Kits for performing such assays in high throughput formats are also available from Cell Signaling Technologies of Beverly, Mass. (see, e.g., PathScan™ Phospho-p44/42 MAPK (T202/Y204) Sandwich ELISA Kit).

Similar Western blotting and ELISA techniques could be used to detect the presence of proteins that are components of the MAPK pathway downstream of the phosphorylation of ERK1 and ERK2 using antibodies that specifically recognize the components that are involved in the pathway. For example, phosphorylation of p90RSK can be assessed using commercially available phosphor-specific antibodies analogous to western detection of phosphorylated ERK2 or ERK2.

In addition, other events downstream of CCX-CKR2 activation can also be monitored to determine signaling activity. Downstream events include those activities or manifestations that occur as a result of stimulation of a chemokine receptor. Exemplary downstream events include, e.g., changed state of a cell (e.g., from normal to cancer cell or from cancer cell to non-cancerous cell). Cell responses include adhesion of cells (e.g., to endothelial cells). Established signaling cascades involved in angiogenesis (e.g., VEGF-mediated signaling) can also be monitored for effects caused by CCX-CKR2 modulators. Chorioallantoic membrane assays (CAM) for example, can be used to assay for effects on angiogenesis or, e.g., the Miles assay to study effects on vascular permeability.

In another example, cell survival may be measured as a surrogate for CCX-CKR2 activity. As described in greater detail in the examples, expression of CCX-CR2 results in extended cell survival of CCX-CR2-expressing cells grown in low serum conditions as compared to cells not expressing CCX-CR2 grown under the same conditions. Thus, antagonism of CCX-CR2 is expected to reduce cell survival, whereas activation (e.g., via agonists) is expected to increase cell survival. Consequently, cell survival and apoptosis can serve as a readout for CCX-CR2 activity.

A wide variety of cell death and apoptosis assays can be incorporated into screening methods to identify modulators of CCX-CR2. In general, assays of this type typically involve subjecting a population of cells to conditions that induce cell death or apoptosis, usually both the in the presence and absence of a test compound that is a potential modulator of cell death or apoptosis. An assay is then conducted with the cells, or an extract thereof, to assess what effect the test agent has on cell death or apoptosis by comparing the extent of cell death or apoptosis in the presence and absence of the test agent. Instead of assaying for cell death or apoptosis, the opposite type of assay can be performed, namely assaying for cell survival, as well as related activities such as cell growth and cell proliferation. Regardless of the particular type of assay, some assays are conducted in the presence of a ligand that activates CCX-CR2 such as I-TAC or SDF-1.

A variety of different parameters that are characteristic of cell death and apoptosis can be assayed for in the present screening methods. Examples of such parameters include, but are not limited to, monitoring activation of cellular pathways for toxicological responses by gene or protein expression analysis, DNA fragmentation, changes in the composition of cellular membranes, membrane permeability, activation of components of death-receptors or downstream signaling pathways (e.g., caspases), generic stress responses, NF-kappa B activation and responses to mitogens.

In view of the role that CCX-CKR2 plays in reducing apoptosis, another approach is to assay for the opposite of apoptosis and cell death, namely to conduct screens in which cell survival or cell proliferation is detected. Cell survival can be detected, for instance, by monitoring the length of time that cells remain viable, the length of time that a certain percentage of the original cells remain alive, or an increase in the number of cells. These parameters can be monitored visually using established techniques.

Another assay to assess apoptosis involves labeling cells with Annexin V (conjugated to Alexa Fluor(r) 488 dye) and Propidium Iodide (PI) (Molecular Probes, Eugene Oreg.). PI, a red fluorescent nucleic acid-binding dye, is impermeant to both live and apoptotic cells. PI only labels necrotic cells by tightly biding to the nucleic acids in the cell. Annexin V takes advantage of the fact that apoptotic cells translocate phosphatidylserine (PS) to the external surface of the cell. Annexin V is a human anti-coagulant with high affinity for (PS). Apoptotic cells, but not live cells, express PS on their outer surface. Annexin V (labeled with Alexa Fluor(r) 488 dye) labels these cells with green fluorescence. Cells can then be analyzed on a fluorescence activated cell sorter (FACS) to assess the fluorescence in the red and green channels: apoptotic cells (Annexin positive, PI negative) fluoresce only in the green channel; live cells (Annexin negative, PI negative) exhibit low fluorescence in both the red and green channels; and necrotic or dead cells (Annexin positive, PI positive) are strongly positive in both the red and green channels.

Other screening methods are based on the observation that expression of certain regulatory proteins is induced by the presence or activation of CCX-CR2. Detection of such proteins can thus be used to indirectly determine the activity of CCX-CR2. As described in greater detail in the examples below, a series of ELISA investigations were conducted to compare the relative concentration of various secreted proteins in the cell culture media for cells transfected with CCX-CR2 and untransfected cells. Through these studies it was determined that CCX-CR2 induces the production of a number of diverse regulatory proteins, including growth factors, chemokines, metalloproteinases and inhibitors of metalloproteinases. Thus, some of the screening methods that are provided involve determining whether a test agent modulates the production of certain growth factors, chemokines, metalloproteinases and inhibitors of metalloproteinases by CCX-CR2. In some instances, the assays are conducted with cells (or extracts thereof) that have been grown under limiting serum conditions as this was found to increase the production of the CCX-CR2-induced proteins (see examples).

The following proteins are examples of the various classes of proteins that were detected, as well as specific proteins within each class: (1) growth factors (e.g., GM-CSF); (2) chemokines (e.g., RANTES, MCP-1); (3) metalloproteinase (e.g., MMP3); and (4) inhibitor of metalloproteinase (e.g., TIMP-1). It is expected that other proteins in these various classes can also be detected.

These particular proteins can be detected using standard immunological detection methods that are known in the art. One approach that is suitable for use in a high-throughput format, for example, are ELISAs that are conducted in multi-well plates. An ELISA kit for detecting TIMP-1 is available from DakoCytomation (Product Code No. EL513). Further examples of suppliers of antibodies that specifically bind the proteins listed above are provided in the examples below. Proteins such as the metalloproteinases that are enzymes can also be detected by known enzymatic assays.

In other embodiments, potential modulators of CCX-CK2 are tested for their ability to modulate cell adhesion. Tumor cell adhesion to endothelial cell monolayers has been studied as a model of metastatic invasion (see, e.g., Blood and Zetter, *Biovhem. Biophys. Acta*, 1032, 89-119 (1990). These monolayers of endothelial cells mimic the lymphatic vasculature and can be stimulated with various cytokines and growth factors (e.g., TNFalpha and IL-1beta). Cells expressing CCX-CKR2 can be evaluated for the ability to adhere to this monolayer in both static adhesion assays as well as assays where cells are under flow conditions to mimic the force of the vasculature in vivo. Additionally, assays to evaluate adhesion can also be performed in vivo (see, e.g., von Andrian, U. H. *Microcirculation.* 3(3):287-300 (1996)).

4. Validation

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a disease model for humans and then determining if the disease (e.g., cancer) is in fact modulated and/or the disease or condition is ameliorated. The animal models utilized in validation studies generally are mammals of any kind. Specific examples of suitable animals include, but are not limited to, primates, mice, rats and zebrafish.

B. Agents That Interact With CCX-CKR2

Modulators of CCX-CKR2 (e.g., antagonists or agonists) can include, e.g., antibodies (including monoclonal, humanized or other types of binding proteins that are known in the art), small organic molecules, siRNAs, CCX-CKR2 polypeptides or variants thereof, chemokines (including but not limited to SDF-1 and/or I-TAC), chemokine mimetics, chemokine polypeptides, etc.

The agents tested as modulators of CCX-CKR2 can be any small chemical compound, or a biological entity, such as a polypeptide, sugar, nucleic acid or lipid. Alternatively, modulators can be genetically altered versions, or peptidomimetic versions, of a chemokine or other ligand. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5 H-bond donors (expressed as the sum of OHs and NHs); having a molecular weight over 500; having a LogP over 5 (or MLogP over 4.15); and/or having more than 10 H-bond acceptors (expressed as the sum of Ns and Os). See, e.g., Lipinski et al. *Adv Drug Delivery Res* 23:3-25 (1997). Compound classes that are substrates for biological transporters are typically exceptions to the rule.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks." For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

CCX7923 (see, FIG. 4) is commercially available and can be made by the condensation of N-[3-(dimethylamino)propyl]-N,N-dimethyl-1,3-propanediamine with bromomethylbicyclo(2,2,1)hept-2-ene by methods known in the art. CCX0803 (see, FIG. 4) is commercially available and can be made by condensation of 3-(2-bromoethyl)-5-phenylmethoxy-indole and 2,4,6-triphenylpyridine by methods well known in the art. See, e.g., *Organic Function Group Preparations,* 2nd Ed. Vol. 1, (S. R. Sandler & W. Karo 1983);

Handbook of Heterocyclic Chemistry (A. R. Katritzky, 1985); Encyclopedia of Chemical Technology, 4th Ed. (J. I. Kroschwitz, 1996).

In one embodiment, the active compounds (i.e., CCX-CKR2 modulators) of the present invention have the general structure (I):

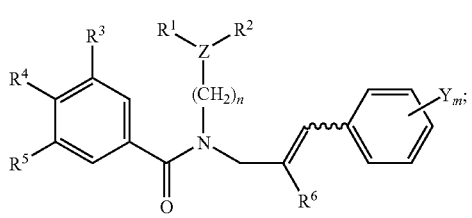

m is an integer from 1 to 5 and each Y that substitutes the benzyl ring is independently selected from the group consisting of hydrogen, alkyl, halo substituted alkyl, alkylene, alkenyl, alkynyl, cycloalkyl, cycloalkylene, halogen, heterocyclic, aryl, arylene, heteroaryl, heteroarylene, hydroxy, alkoxy, and aryloxy, n is 0, 1, 2 or 3;

Z is —CH— or —N—;

$R^1$ and $R^2$ are each independently alkyl or hydrogen, or Z in combination with $R^1$ and $R^2$ form a 5- or 6-membered ring comprising at least one nitrogen and optionally comprising one or more additional heteroatoms, where said 5-6-membered ring is optionally and independently substituted with one or more moieties selected from the group consisting of alkyl, alkenyl, phenyl, benzyl, sulfonyl, and substituted heteroatom;

$R^3$, $R^4$, and $R^5$ are each independently selected from the group consisting of hydrogen, alkyl, halo substituted alkyl, alkylene, alkenyl, alkynyl, cycloalkyl, cycloalkylene, heterocyclic, aryl, arylene, heteroaryl, heteroarylene, hydroxy, alkoxy, and aryloxy; and $R^6$ is alkyl or hydrogen;

provided that if Z is nitrogen and $R^1$ and $R^2$ together with Z form a morpholinyl group, then n is 3, and at least one of $R^3$, $R^4$, and $R^5$ is hydroxy, alkoxy, or aryloxy; or provided that if n=1, Z is carbon and $R^1$ and $R^2$ is combination is not —CH$_2$CH$_2$NCH$_2$CH$_2$—; or provided that if $R^1$ together with $R^2$ is —CH(CH$_3$)(CH$_2$)$_4$—, then Z is —CH—; or provided that if $R^5$ is t-butyl, then $R^3$ is hydrogen; or provided that if $R^4$ and $R^5$ together form a 5-membered ring, then at least one of the atoms bonded to the phenyl ring is carbon. See, U.S. Provisional patent application No. 60/434,912, filed Dec. 20, 2002 and U.S. Provisional patent application No. 60/516,151, filed Dec. 20, 2003.

The wavy bond connecting the olefin to the substituted phenyl ring signifies that the ring may be either cis or trans to $R^6$. In a preferred embodiment, n is 1, 2, or 3. In another preferred embodiment, n is 2 or 3. In a further preferred embodiment, n is 3.

In another embodiment, preferred compounds have the general structure (I), where $R^6$ is hydrogen. In a further embodiment, preferred compounds have the general structure (I), where $R^6$ is methyl.

In another embodiment, preferred compounds have the general structure (I), where $R^3$, $R^4$, and $R^5$ are independently hydrogen, hydroxy, alkyl, alkoxy, aryloxy, and halo substituted alkyl. More preferably, $R^3$, $R^4$, and $R^5$ are independently alkoxy or hydrogen. In another embodiment, preferred compounds have the general structure (I), where $R^4$ is hydrogen and $R^3$ and $R^5$ are alkoxy (—OR), including trifluoroalkoxy groups such as trifluoromethoxy and (—OCH$_2$CF$_3$). In a further embodiment, $R^3$ is hydrogen and $R^4$ and $R^5$ are alkoxy. In either of these embodiments, the alkoxy group may be methoxy (—OCH$_3$) or ethoxy (—OCH$_2$CH$_3$).

In another embodiment, preferred compounds have the general structure (I), where $R^4$ and $R^5$ together form a heterocyclic, aryl, or heteroaryl ring. In another preferred embodiment, $R^3$ is hydrogen and $R^4$ and $R^5$ together are —O(CH$_2$)$_3$O—, —(CH)$_4$—, or —N(CH)$_2$N—.

In another embodiment, preferred compounds have the general structure (I), where Z is nitrogen and Z in combination with $R^1$ and $R^2$ form a heteroaryl or heterocyclic group. In a preferred embodiment, compounds have the general structure (I), where Z is CH and Z in combination with $R^1$ and $R^2$ form a heteroaryl or heterocyclic group. More preferable compounds have the general structure (I), where Z is CH and Z in combination with $R^1$ and $R^2$ form a heterocyclic group containing nitrogen. In a further embodiment, Z in combination with $R^1$ and $R^2$ form a substituted or unsubstituted morpholinyl, pyrrolidinyl, piperidinyl, or piperazinyl group.

Preferred substituents for the heteroaryl or heterocyclic group include alkyl, alkenyl, alkynyl, cycloalkyl, aryl, aralkyl, heteroaryl, alkoxy, hydroxy, heteroatoms, and halides. In an especially preferred embodiment, the heteroaryl or heterocyclic group is substituted with benzyl, phenyl, methyl, ethyl, cyclohexyl, methoxy-methyl (—CH$_2$OCH$_3$), or cyclohexyl-methyl (—CH$_2$(C$_6$H$_{11}$)) groups.

In one embodiment, a preferred compound has the general structure (I), where Z in combination with $R^1$ and $R^2$ is an alkyl- or methoxy-methyl-substituted pyrrolidinyl group; a benzyl-, phenyl-, methyl-, ethyl-, or substituted heteroatom substituted piperidinyl group; or a benzyl-, phenyl-, or sulfonyl-substituted piperazinyl group. Especially preferred substituted heteroatom groups include alkoxy, aminyl, cycloalkyl aminyl, alkyl aminyl, cyclopropyl aminyl, isopropyl aminyl, benzyl aminyl, and phenoxy. Preferably, the substituted heteroatom is at the 3 position of the piperidinyl ring.

In another aspect, preferred compounds have the general structure (I), where Z in combination with $R^1$ and $R^2$ is

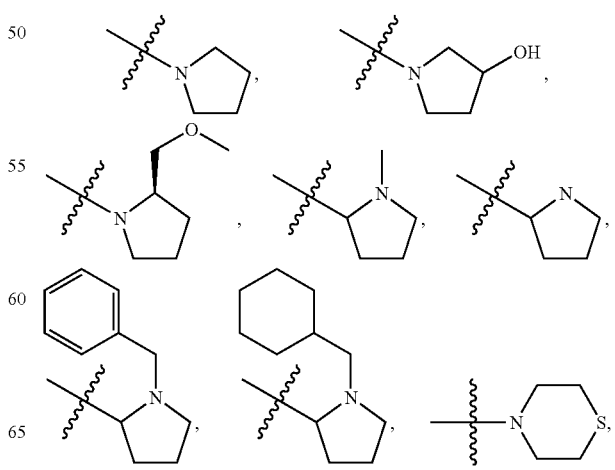

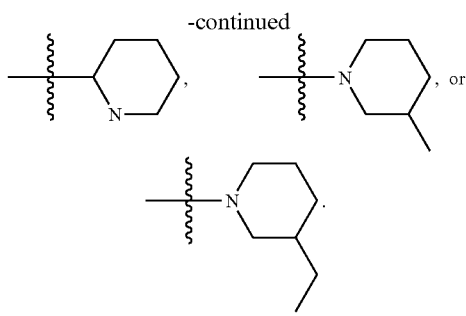

Preferred compounds having the general structure (I) can also have Z as a nitrogen atom, have $R^1$ and $R^2$ each as alkyl or methyl groups, or have $R^1$ and $R^2$ together forming —C(C(O)N(CH$_3$)$_2$)(CH$_2$)$_3$—.

In another embodiment, Z in combination with $R^1$ and $R^2$ form a 5-membered ring including nitrogen and optionally including one or more additional heteroatoms. In this embodiment, n is preferably 1 and Z is preferably —CH—. In an especially preferred embodiment of this type, Z in combination with $R^1$ and $R^2$ is

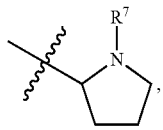

where $R^7$ is preferably hydrogen, alkyl, aryl, or aralkyl.

In another preferred embodiment $R^7$ can be a halogenated benzyl or phenyl group. In a further embodiment, $R^7$ is preferably hydrogen, methyl, ethyl, benzyl, or para-fluoro-phenyl.

In another embodiment, the active compounds of the present invention have the general structure (II):

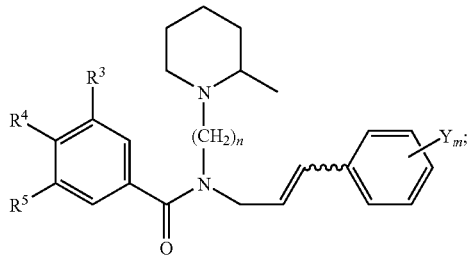

where
m is an integer from 1 to 5;
each Y that substitutes the benzyl ring is independently selected from the group consisting of hydrogen, alkyl, halo substituted alkyl, alkylene, alkenyl, alkynyl, cycloalkyl, cycloalkylene, halogen, heterocyclic, aryl, arylene, heteroaryl, heteroarylene, hydroxy, and alkoxy;
n is 1, 2 or 3; and
$R^3$, $R^4$, and $R^5$ are each independently selected from the group consisting of hydrogen, alkyl, halo substituted alkyl, alkylene, alkenyl, alkynyl, cycloalkyl, cycloalkylene, heterocyclic, aryl, arylene, heteroaryl, heteroarylene, hydroxy, alkoxy, and aryloxy.

As in structure (I) above, the wavy bond connecting the olefin to the substituted phenyl ring signifies that the ring may be either cis or trans.

In another embodiment, preferred compounds may have the general structure (II), where n is 3. In another embodiment, preferred compounds may have the general structure (II), where $R^3$, $R^4$, and $R^5$ are substituted as described for structure (I) above. At present, especially preferred compounds have the general structure (II), where $R^3$, $R^4$, and $R^5$ are alkoxy or methoxy.

While many synthetic routes known to those of ordinary skill in the art may be used to synthesize the active compounds of the present invention, a general synthesis method is given below in Scheme I.

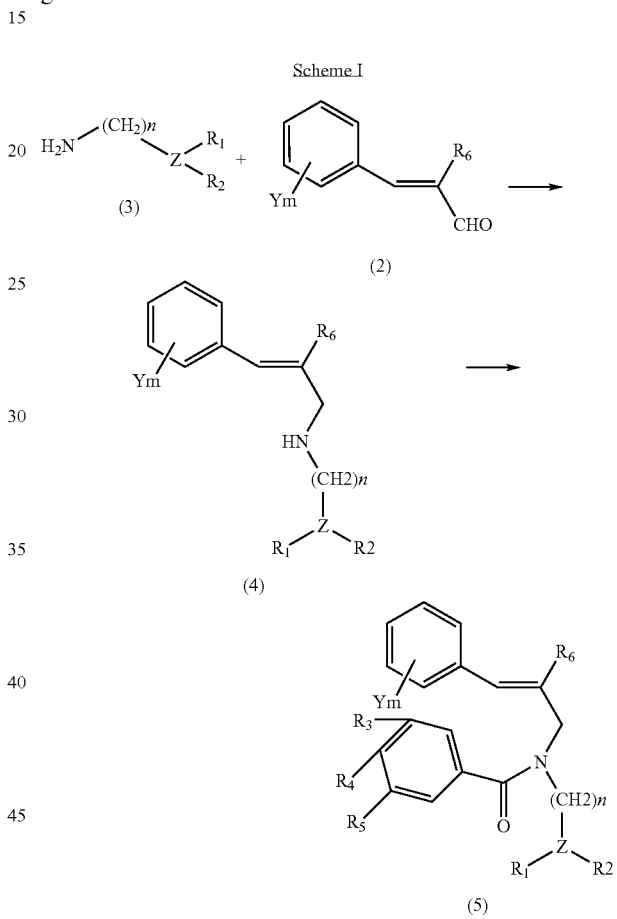

In Scheme I, aldehyde (2) undergoes a condensation reaction with primary amine (3) via reductive amination. Suitable primary amines are commercially available from Aldrich, Milwaukee, Wis., for example, or may be synthesized by chemical routes known to those of ordinary skill in the art.

The amination reaction may be carried out with a reducing agent in any suitable solvent, including, but not limited to tetrahydrofuran (THF), dichloromethane, or methanol to form the intermediate (4). Suitable reducing agents for the condensation reaction include, but are not limited to, sodium cyanoborohydride (as described in Mattson, et al., J. Org. Chem. 1990, 55, 2552 and Barney, et al., Tetrahedron Lett. 1990, 31, 5547); sodium triacethoxyborohydride (as described in Abdel-Magid, et al., Tetrahedron Lett. 31:5595 (1990)); sodium borohydride (as described in Gribble; Nutaitis Synthesis. 709 (1987)); iron pentacarbonyl and alcoholic KOH (as described in Watabane, et al., Tetrahedron Lett. 1879

(1974)); and $BH_3$-pyridine (as described in Pelter, et al., *J. Chem. Soc.*, Perkin Trans. 1:717 (1984)).

The transformation of intermediate (4) to compound (5) may be carried out in any suitable solvent, such as tetrahydrofuran or dichloromethane, with a suitably substituted acyl chloride in presence of a base. Tertiary amine bases are preferred. Especially preferred bases include triethylamine and Hunnings base.

Alternatively, the transformation of intermediate (4) to compound (5) can also be obtained with a suitable coupling reagent, such as 1-ethyl-3-(3-dimethylbutylpropyl)carbodiimide carbodiimide or Dicyclohexyl-carbodiimide (as described in B. Neises and W. Steglich, Angew. *Chem., Int. Ed. Engl.* 17:522 (1978)), in the presence of a catalyst, such as 4-N,N-dimethylamino-pyridine, or in the presence of hydroxybenzotriazole (as described in K. Horiki, *Synth. Commun.* 7:251).

To demonstrate that the compounds described above are useful antagonists for SDF-1 and I-TAC chemokines, the compounds were screened in vitro to determine their ability to displace SDF-1 and I-TAC from the CCX-CKR2 receptor at multiple concentrations. The compounds were combined with mammary gland cells expressing CCX-CKR2 receptor sites in the presence of the $^{125}$I-labeled SDF-1 and/or $^{125}$I I-TAC chemokine. The ability of the compounds to displace the labeled SDF-1 or I-TAC from the CCX-CKR2 receptor cites at multiple concentrations was then determined with the screening process.

Compounds that were deemed effective SDF-1 and I-TAC antagonists were able to displace at least 50% of the SDF-1 and/or I-TAC chemokine from the CCX-CKR2 receptor at concentrations at or below 1.1 micromolar (µM) and more preferably at concentrations at or below 300 nanomolar (nM). In some cases, it is desirable that compounds can displace at least 50% of the SDF-1 and/or I-TAC from the CCX-CKR2 receptor at concentrations at or below 200 nM. Exemplary compounds that met these criteria are reproduced in Table I below.

TABLE I

| No. | Compound |
|-----|----------|
| 1 | |
| 2 | |
| 3 | |
| 4 | |

TABLE I-continued

| No. | Compound |
|---|---|
| 5 | |
| 6 | |
| 7 | |
| 8 | |
| 9 | |
| 10 | |
| 11 | |
| 12 | |
| 13 | |

TABLE I-continued

| No. | Compound |
|-----|----------|
| 14 | |
| 15 | |
| 16 | |
| 17 | |
| 18 | |
| 19 | |
| 20 | |
| 21 | |
| 22 | |
| 23 | |

TABLE I-continued

| No. | Compound |
|---|---|
| 24 | |
| 25 | |
| 26 | |
| 27 | |
| 28 | |
| 29 | |
| 30 | |
| 31 | |

TABLE I-continued

| No. | Compound |
|---|---|
| 32 | |
| 33 | |
| 34 | |
| 35 | |

TABLE I-continued

| No. | Compound |
|---|---|
| 36 | |
| 37 | |
| 38 | |
| 39 | |
| 40 | |

TABLE I-continued

| No. | Compound |
|---|---|
| 41 | |
| 42 | |
| 43 | |
| 44 | |
| 45 | |
| 46 | |
| 47 | |
| 48 | |
| 49 | |
| 50 | |
| 51 | |
| 52 | |

C. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention. More recently, microfluidic approaches to reagent manipulation have been developed.

The invention provides in vitro assays for identifying, in a high throughput format, compounds that can modulate the function or activity of CCX-CKR2. Control reactions that measure CCX-CKR2 activity of the cell in a reaction that does not include a potential modulator are optional, as the assays are highly uniform. Such optional control reactions, however, increase the reliability of the assay.

In some assays it will be desirable to have positive controls to ensure that the components of the assays are working properly. At least two types of positive controls are appropriate. First, a known activator or ligand of CCX-CKR2 can be incubated with one sample of the assay, and the resulting increase in signal resulting from an increased activity of CCX-CKR2 (e.g., as determined according to the methods herein). Second, an inhibitor or antagonist of CCX-CKR2 can be added, and the resulting decrease in signal for the activity of the chemokine receptor can be similarly detected. It will be appreciated that modulators can also be combined with activators or inhibitors to find modulators which inhibit the increase or decrease that is otherwise caused by the presence of the known modulator of CCX-CKR2.

IV. Expressing CCX-CKR2 in a Subject

In some embodiments, CCX-CKR2 is expressed in a subject, thereby increasing expression of CCX-CKR2. Alternatively, inhibitory polynucleotides, including, e.g., siRNA or antisense sequences, may be expressed in vitro or iv vivo to inhibit expression of CCX-CKR2. In some cases, a polynucleotide encoding CCX-CKR2 is introduced into a cell in vitro and the cell is subsequently introduced into a subject. In some of these cases, the cells are first isolated from the subject and then re-introduced into the subject after the polynucleotide is introduced. In other embodiments, polynucleotides encoding CCX-CKR2 are introduced directly into cells in the subject in vivo.

In some cases, the CCX-CKR2-encoding polypeptides are introduced into cells from: (i) a tissue of interest, (ii) exogenous cells introduced into the tissue, or (iii) neighboring cells not within the tissue. In some embodiments, the polynucleotides of the invention are introduced into endothelial cells. The tissue with which the endothelial cells are associated is any tissue in which it is desired to enhance the migration or expansion of endothelia.

Conventional viral and non-viral based gene transfer methods can be used to introduce nucleic acids encoding engineered polypeptides of the invention in mammalian cells or target tissues. Such methods can be used to administer nucleic acids encoding polypeptides of the invention (e.g., CCX-CKR2) to cells in vitro. In some embodiments, the nucleic acids encoding polypeptides of the invention are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered polypeptides of the invention take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression of the polypeptides of the invention is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

pLASN and MFG-S are examples are retroviral vectors that have been used in clinical trials (Dunbar et al., *Blood* 85:3048-305 (1995); Kohn et al., *Nat. Med.* 1: 1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA) encoding a polypeptides of the invention, and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693-1702 (1992)).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989).

V. Diagnosis and Prognosis

The present invention provides methods of detecting a cancer cell, including methods of providing a prognosis or diagnosis of cancer. As demonstrated herein, CCX-CKR2 is expressed in nearly every cancer cell tested to date, whereas normal (non-cancer) expression of CCX-CKR2 appears to be limited to the kidney and some brain cells as well as in certain developmental stages of fetal liver. Therefore, expression of CCX-CKR2 in a cell, and in particular, in a non-fetal cell and/or a cell other than a kidney or brain cell, indicates the likely presence of a cancer cell. In some cases, samples containing CCX-CKR2-expressing cells are confirmed for the presence of cancer cells using other methods known in the art.

According to yet another aspect of the invention, methods for selecting a course of treatment of a subject having or suspected of having cancer are provided. The methods include obtaining from the subject a biological sample, contacting the sample with antibodies or antigen-binding fragments thereof that bind specifically to CCX-CKR2, detecting the presence or absence of antibody binding, and selecting a course of treatment appropriate to the cancer of the subject. In some embodiments, the treatment is administering CCX-CKR2 antagonists to the subject.

Detection methods using agents that bind a protein are well known and include, e.g., various immunoassays, flow cytometry, etc. Using flow cytometry, cells expressing a specific antigen of interest within a mixed population of cells can be identified. Briefly, cells are permitted to react with an antibody specific for the protein of interest (e.g., CCX-CKR2). The antibody can either be fluorescently labeled (direct method of staining), or if it is not labeled, a second antibody that reacts with the first can be fluorescently tagged (indirect method of staining). Cells are then passed through an instrument that can detect the fluorescent signal. Cells are aspirated and made into a single cell suspension. This cell suspension is passed by a laser that excites the fluorochrome labeled antibody now binding to the cells and acquires this data. Cells that are found to be bright (i.e. react with the fluorescently labeled antibody) express the protein of interest; cells that are dull (i.e. do not react with the fluorescently labeled antibody) do not express the protein of interest.

The present invention provides for methods of diagnosing human diseases including, but not limited to cancer, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers); as well as brain and neuronal dysfunction, such as Alzheimer's disease and multiple sclerosis; kidney dysfunction; rheumatoid arthritis; cardiac allograft rejection; atherosclerosis; asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma. As provided herein, including in the examples, normal and diseased cells and tissues can be distinguished based on reactivity to an anti-CCX-CKR2 monoclonal antibody or SDF-1 and I-TAC. For example, cancer cells are detected by detecting on a cell a chemokine receptor for which SDF-1α and I-TAC compete for binding.

In addition, differences in ligand binding between chemokine receptors can be detected and such differences can be used to detect cells expressing CCX-CKR2. For example, no other chemokine receptor has both SDF1 and I-TAC as ligands. Chemokine binding can be determined using tissue samples (e.g., biopsies) or can be monitored directly in a tissue in situ (e.g., using radiolabelled chemokine imaging).

Immunoassays can also be used to qualitatively or quantitatively analyze CCX-CKR2. A general overview of the applicable technology can be found in Harlow & Lane, *Antibodies: A Laboratory Manual* (1988). Alternatively, non-antibody molecules with affinity for CCX-CKR2 can also be used to detect the receptor.

Methods for producing polyclonal and monoclonal antibodies that react specifically with a protein of interest are known to those of skill in the art (see, e.g. Coligan, *Current Protocols in Immunology* (1991); Harlow & Lane, *Antibodies, A Laboratory Manual* (1988); Goding, *Monoclonal Antibodies: Principles and Practice* (2d ed. 1986); and Kohler and Milstein *Nature,* 256:495-497 (1975)). Such techniques include antibody preparation by selection of antibodies from libraries of recombinant antibodies in phage or similar vectors. For example, in order to produce antisera for use in an immunoassay, the protein of interest or an antigenic fragment thereof, is isolated as described herein. For example, a recombinant protein is produced in a transformed cell line. An inbred strain of mice, rats, guinea pigs or rabbits is immunized with the protein using a standard adjuvant, such as Freund's adjuvant, and a standard immunization protocol. Alternatively, a synthetic peptide derived from the sequences disclosed herein and conjugated to a carrier protein can be used as an immunogen. A further option is to use a cell expressing the protein or a membrane fraction or liposome comprising CCX-CKR2 or a fragment thereof as an antigen. Antibodies raised against the cell, membrane fraction or liposome can then be selected for their ability to bind to the protein.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their crossreactivity against a different, and sometimes, homologous proteins, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better to CCX-CKR2.

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3rd ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Such antibodies are useful for both detection and therapeutic applications. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239: 1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

VI. Methods of Treatment, Administration And Pharmaceutical Compositions

Modulators of CCX-CKR2 (e.g., antagonists or agonists) can be administered directly to the mammalian subject for modulation of chemokine receptor signaling in vivo. In some embodiments, the modulators compete with SDF1 and/or I-TAC for binding to CCX-CKR2. Modulation of CCX-CKR2 can include, e.g., antibodies (including monoclonal, humanized or other types of binding proteins that are known in the art), small organic molecules, siRNAs, etc.

In some embodiments, the CCX-CKR2 modulators are administered to a subject having cancer. In some cases, CCX-CKR2 modulators are administered to treat cancer, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers); as well as brain and neuronal dysfunction, such as Alzheimer's disease and multiple sclerosis; kidney dysfunction; rheumatoid arthritis; cardiac allograft rejection; atherosclerosis; asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma. Since CCX-CKR2 if often expressed in cancer cells but not non-cancer cells, it is typically desirable to administer antagonists of CCX-CKR2 to treat subjects having cancer. In some cases, the modulators have a molecular weight of less than 1,500 daltons, and in some cases less than 1,000, 800, 600, 500, or 400 daltons.

Administration of the modulators can be by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The modulators (e.g., agonists or antagonists) of the expression or activity of CCX-CKR2, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

In some embodiments, CCX-CKR2 modulators of the present invention can be administered in combination with other appropriate therapeutic agents, including, e.g., chemotherapeutic agents, radiation, etc. Selection of the appropriate agents for use in combination therapy may be made by one of ordinary skill in the art, according to conventional pharmaceutical principles. The combination of therapeutic agents may act synergistically to effect the treatment or prevention of the various disorders such as, e.g., cancer, kidney dysfunction, brain dysfunction or neuronal dysfunction. Using this approach, one may be able to achieve therapeutic efficacy with lower dosages of each agent, thus reducing the potential for adverse side effects.

The dose administered to a patient, in the context of the present invention should be sufficient to effect a beneficial response in the subject over time (e.g., to reduce tumor size or tumor load). The optimal dose level for any patient will depend on a variety of factors including the efficacy of the specific modulator employed, the age, body weight, physical activity, and diet of the patient, on a possible combination with other drugs, and on the severity of a particular disease. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, chemokine receptor modulators of the present invention can be administered at a rate determined by the LD-50 of the modulator, and the side-effects of the modulator at various concentrations, as applied to the mass and overall health of the subject. Administration can be accomplished via single or divided doses.

VII. Compositions, Kits, Integrated Systems and Proteomic Applications

The invention provides compositions, kits and integrated systems for practicing the assays described herein using anti-CCX-CKR2 antibodies or other agents that specifically detect CCX-CKR2.

The invention provides assay compositions for use in solid phase assays; such compositions can include, for example, a CCX-CKR2 polypeptide (including, e.g., as part of a cell, membrane fractions or liposomes (see, e.g., Babcok et al., *J. Biol. Chem.* 276(42):38433-40 (2001); Mirzabekov et al., *Nat. Biotechnol.* 18(6):649-54 (2000))) immobilized on a solid support, and a labeling reagent. In each case, the assay compositions can also include additional reagents that are desirable for hybridization. For example, the solid support can be, e.g., a petri plate, multi-well plate or microarray. In addition, microarrays of peptide libraries can be used to identify peptide sequences that specifically bind CCX-CKR2.

Agents that specifically bind to CCX-CKR2 can also be included in the assay compositions. For example, an antibody that specifically binds to CCX-CKR2 can be immobilized on a solid support. In some of these embodiments, the agent is used to detect the presence or absence of CCX-CKR2 or cells expressing CCX-CKR2. For example, the solid support can be petri plate, multi-well plate or microarray.

The invention also provides kits for carrying out the assays of the invention. The kits typically include an agent (e.g., an antibody or other small molecule) that specifically binds to CCX-CKR2 and a label for detecting the presence of the agent. The kits may include one or more other chemokine receptor polypeptides. Kits can include any of the compositions noted above, and optionally further include additional components such as instructions to practice a high-throughput method of assaying for an effect on activity or function of chemokine receptors, one or more containers or compartments (e.g., to hold the probe, labels, or the like), a control modulator of the function or activity of chemokine receptors, a robotic armature for mixing kit components or the like.

In some embodiments, the kits comprise SDF1 and/or I-TAC. In some embodiments, the kits comprise a labeled or tagged SDF-1 and cold competitor I-TAC or alternatively, a labeled or tagged I-TAC and cold competitor SDF-1. The labeled or tagged chemokine can be labeled or tagged in any way known to those of skill in the art. In some embodiments, the labeled chemokine is radiolabeled or tagged with biotin or a fluorescent label. Alternatively, or in addition, the kit can contain an anti-I-TAC binding reagent (e.g., an antibody) for detection of I-TAC. The kits can also contain the appropriate salt buffers and other reagents to perform a competitive binding assay, e.g., on intact cells or cell membranes. Such reagents are described in, e.g., the examples below. In some aspects, the kits also comprise a solid support or receptacle for measuring ligand binding to CCX-CKR2 (e.g., in a plate format for reactions compatible with scintillation counters or automated plate readers). In some aspects, the kits comprise instructions for using the kits, e.g., in the methods of the invention.

The invention also provides integrated systems for high-throughput screening of potential modulators for an effect on the activity or function of potential CCX-CKR2 modulators. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image.

EXAMPLES

Example 1

This example shows that SDF-1 and I-TAC compete for binding to a new chemokine receptor.

Materials and Methods.

Reagents and Cells. Human, viral and murine recombinant chemokines were obtained from R&D Systems (Minneapolis, Minn.) and PeproTech (Rocky Hill, N.J.) where indicated. 125 I-labeled SDF-1a was purchased from PerkinElmer Life Sciences, Inc. (Boston, Mass.) and 125 I-labeled I-TAC was obtained from Amersham Pharmacia Biotech (Buckinghamshire, UK). Monoclonal antibodies used in flow cytometry and ligand binding competition were from R&D Systems (Minneapolis, Minn.): anti-CXCR4 clones 12G5, 44708.111 (171), 44716.111 (172), 44717.111 (173), nmIgG2a, and nmIgG2b. The secondary anitbody, goat anti-mouse IgG PE conjugate (Coulter Immunotech, Miami, Fla.), was used to detect antibody binding by flow cytometry. The following cells were obtained from the American Type Culture Collection (Manassas, Va.): MCF-7 (adenocarcinoma; mammary gland), MDA MB-231 (adenocarcinoma; mammary gland), MDA MB-435s (ductal carcinoma; mammary gland), DU 4475 (mammary gland), ZR 75-1 (ductal carcinoma; mammary gland), HEK 293 (human embryonic kidney), HUVEC-C (human umbilical vein; vascular endothelium; normal). CEM-NKr (acute lymphoblastic leukemia; peripheral blood; T lymphoblast) cells were obtained from the NIH AIDS Research and Reference Reagent Program. Cell lines were cultured in DMEM (Mediatech, Herndon, Va.) supplemented with 10% fetal bovine serum (FBS) (HyClone Logan, Utah) at 37° C. in a humidified incubator at a 5% $CO_2$/air mixture. Human peripheral blood mononuclear cells (PBMC) were obtained from buffy coats of healthy donors (Stanford Blood Center, Palo Alto, Calif.) by centrifugation on Ficoll-Hypaque density gradients. Isolated PBMC were activated with 2.5 ug/ml phytohemagglutnin (PHA) (Sigma Chemical Company, St. Louis, Mo.) and 10 ng/ml recombinant human IL-2 (R&D Systems, Minneapolis, Minn.) for 3 days in RPMI-1640 (Mediatech, Herndon, Va.) supplemented with 10% FBS at 37° C. in a humidified incubator at a 5% $CO_2$/air mixture. After activation, the cells were washed and cultured in RPMI supplemented with 10% FBS and 10 ng/ml IL-2, which was replenished every 3-4 days until the day cells were used.

Binding Analysis. We employed our technique, "DisplaceMax™", to examine the global profile of chemokine ligand interaction with the SDF1 receptoron MCF-7 and CEM-NKr cells. This technology employs expanded, efficiency-maximized radioligand binding using filtration protocols as described previously (Dairaghi, et al. *J Biol Chem* 274:21569-74 (1999); Gosling, J. et al. *J Immunol* 164:2851-6 (2000)). In these assays, DisplaceMax™ employed the simultaneous interrogation of MCF-7 or CEM-NKr cells, as indicated, by >110 distinct purified chemokines in the ability to displace $^{125}I$ radiolabeled SDF-1α or I-TAC, as indicated, using the protocol described (Dairaghi, et al. *J Biol Chem* 274:21569-74 (1999); Gosling, J. et al. *J Immunol* 164:2851-6 (2000)). Briefly, chemokine elements were incubated with cells followed by the addition of radiolabeled chemokine ($^{125}I$ SDF-1a or $^{125}I$ h I-TAC) for 3 hr at 4° C. in the following binding medium (25 mM HEPES, 140 mM NaCl, 1 mM $CaCl_2$, 5 mM $MgCl_2$ and 0.2% bovine serum albumin, adjusted to pH 7.1). Small molecules were included in some assays, where indicated. In these assays the compound was added to the plate to the indicated concentration followed by the addition of radiolabeled chemokine. All assays were then incubated for 3 hrs at 4° C. with gentle agitation. Following incubation in all binding assays, reactions were aspirated onto PEI-treated GF/B glass filters (Packard) using a cell harvester (Packard) and washed twice (25 mM HEPES, 500 mM NaCl, 1 mM $CaCl_2$, 5 mM $MgCl_2$, adjusted to pH 7.1). Scintillant (MicroScint 10, Packard) was added to the wells, and the filters were counted in a Packard Topcount scintillation counter. Data were analyzed and plotted using Prism (GraphPad Prism version 3.0a for Macintosh, GraphPad Software).

Determination of $^{125}I$ SDF-1α Receptor Binding. Using the filtration based assay described above, cells were pre-incubated with either 1) buffer alone, 2) excess SDF-1β (90 nM final) or 3) MIG (175 nM final) as indicated for 30 min at 4° C. Following this incubation the indicated cold chemokine competitor at stated concentrations and $^{125}I$ h I-TAC were added to the binding reactions. All assays were then incubated, harvested and analyzed as described above.

RT PCR. mRNA was isolated from cells using standard techniques. Complementary DNA was analyzed for the expression of CXCR3 and CXCR4 by PCR. Specific primers were obtained from Integrated DNA Technologies (Coralville, Iowa). Specific PCR products were measured by means of a Hybaid Omn-E (E&K Scientific Products, Inc., Saratoga, Calif.) during 35 cylces. GAPDH was measured as a control.

Adhesion Assay. HUVEC cells were grown overnight on tissue culture treated slides in the presence of TNFα (25 ng/ml) and IFNγ (50 ng/ml). The following day NSO transfected CCX-CKR2 cells as well as wildtype controls were labeled with calcein-AM. The calcein labeled cells were then plated onto the endothelial monolayer in the presence and absence of CCX-CKR2 anatgonist (CCX3451). Slides were incubated at 37° C. for 40 minutes followed by washing with PBS to remove non-adherent cells. Adherent NSO cells were visualized by fluorescent microscopy. Cells treated with compound or vehicle were counted by eye from three fields of view (fov) and plotted.

Results

Recent reports have identified CXCR4 expression on several tumor cell types (Sehgal, et al., *J Surg Oncol* 69:99-104 (1998); Sehgal, A., et al. *J Surg Oncol* 69:239-48 (1998); Burger, et al. *Blood* 94:3658-67 (1999); Rempel, et al. *Clin Cancer Res* 6:102-11 (2000); Koshiba, T. et al. *Clin Cancer Res* 6:3530-5 (2000); Muller, A. et al. *Nature* 410:50-6 (2001); Robledo, et al. *J Biol Chem* 276:45098-45105 (2001)) and in one example link this expression with breast tumor cell metastasis (Muller, A. et al. *Nature* 410:50-6 (2001)). To further investigate the role of chemokine receptors on tumor cells we undertook to evaluate the expression of CXCR4 on several human breast tumor cell lines. Initially the pattern of CXCR4 expression was evaluated by flow cytometry. Primary IL-2 cultured T lymphocytes and two T cell lines, CEM-NKr and Jurkat, were examined to determine the T cell phenotype of anti-CXCR4 staining. Three breast tumor cell lines, MCF-7, MDA MB-231 and MDA MB-435s, were also tested. All four anti-CXCR4 clones tested stained T cells. Surprisingly, while breast tumor cells are reported to express CXCR4, the widely used clone 12G5 did not detect any CXCR4 on the breast tumor cells. Weak and variable reactivity was detected with the three other clones tested on the breast tumor cells. The breast tumor cell lines DU 4475 and ZR 75-1 were also tested in this assay (data not shown) and found to have similar antibody staining profiles to the other breast tumor cells tested. Thus, the staining patterns of the mAb panel for CXCR4 seem to suggest two distinct types of reactivity: a "leukocyte" CXCR4 phenotype (exemplified by CEM-NKr, Jurkat and IL-2 lymphocyte staining) and a breast tumor cell phenotype (exemplified by weak staining on MCF-7 and MDA MB-231 breast tumor cell lines).

The consistent lack of reactivity using the most widely employed anti-CXCR4 mAb, clone 12G5, on breast tumor cells led us to examine CXCR4 expression in these cells by RT PCR. mRNA was isolated from the three breast tumor lines tested in flow cytometry as well as IL-2 cultured lymphocytes and the T cell lines, CEM-NKr and Jurkat, as positive controls for CXCR4 expression. Despite the lack of reactivity with 12G5 and the variable reactivity with the other anti-CXCR4 clones tested, the breast tumor cell lines, MCF-7 and MDA MB-231, did express CXCR4 message; however, MDA MB-435s was found to be negative for CXCR4 expression. In all cases GAPDH was measured as a control. To examine whether differences in mAb reactivity may be due to sequence differences thus resulting in epitope variations in CXCR4 on various cell lines, we then sequenced the PCR products generated from MCF-7, as a representative CXCR4+ breast tumor cell, and CEM-NKr, as a representative T cell. The sequences from these two cell lines are identical to published CXCR4 sequences suggesting that despite the different CXCR4 antibody profiles, the genetic and thus the polypeptide structure of CXCR4 in both cell types was identical.

We have previously reported a set of techniques by which receptor binding to a comprehensive array of chemokine ligands can be simultaneously assessed (Dairaghi, et al. *J Biol Chem* 274:21569-74 (1999); Gosling, J. et al. *J Immunol* 164:2851-6 (2000)). In this fashion we probed the CXCR4 binding profile on CEM-NKr as compared to MCF-7 cells. Greater than 90 chemokine elements were tested for the ability to displace the signature chemokine, $^{125}$I SDF-1α, for binding to CEM-NKr (FIG. 1) or MCF-7 cells (FIG. 1). As expected, the potential high affinity competitors of $^{125}$I SDF-1α on CEM-NKr include hSDF-1β and mSDF-1, while hSDF-1α and HHV8 vMIP-II exhibit potential moderate affinity competition. This is consistent with all previously reported results of SDF-1 as the only non-viral ligand for CXCR4. However, the overall pattern of competition on MCF-7 cells was markedly different. In this cell type hI-TAC and mI-TAC demonstrated high affinity competition for the same signature ligand SDF-1. To further investigate this unusual result $^{125}$I I-TAC was tested as the signature ligand on MCF-7 cells (FIG. 1). The high affinity displacement profile using $^{125}$I I-TAC on MCF-7 was identical to the profile obtained using $^{125}$I SDF-1α. Thus, on MCF-7 cells I-TAC and SDF-1 behave indistinguishably in binding and compete for the same receptor site.

Figure 2:
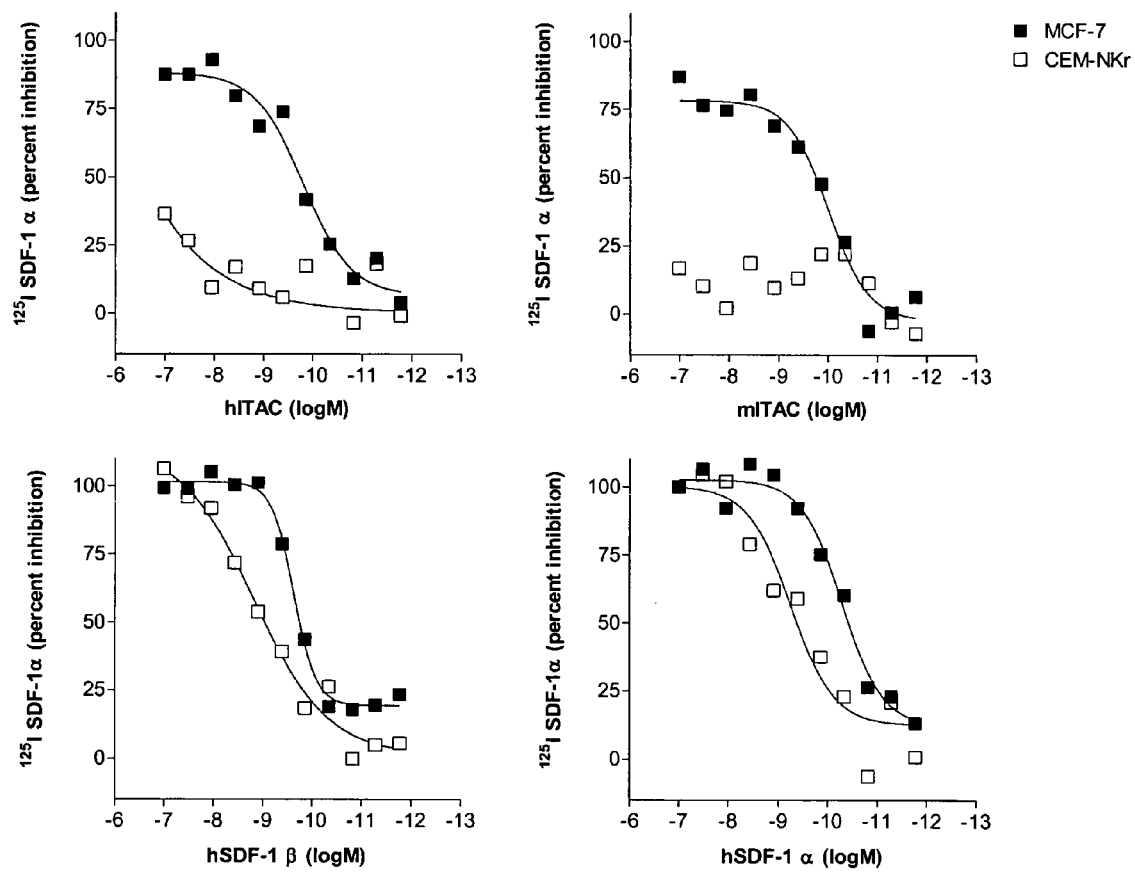
FIG. 2 illustrates a comparison of ligand binding affinity and specificity on CEM-NKr and MCF-7. Selected potential high affinity ligands identified in FIG. 2 were chosen for dose response competition on CEN-NKr (open squares) and MCF-7 (solid squares). In each competition $^{125}$I SDF-1α is in competition with a cold competitor chemokine as indicated.

To characterize further the binding of I-TAC and SDF-1, dose response curves were obtained in competition binding experiments with selected potential high affinity ligands on CEM-NKr and MCF-7. As suggested by the DisplaceMax™ data, I-TAC does compete with $^{125}$I SDF-1α for binding to MCF-7, but not CEM-NKr (FIG. 2). Homologous competition of $^{125}$I SDF-1α with either SDF-1 isoform, SDF-1α or SDF-1β, resulted in complete competition on CEM-NKr and MCF-7 (FIG. 2). Notably, the affinity of SDF-1 for the receptor expressed on MCF-7 is higher than that on CEM-NKr. Thus, while the sequence of CXCR4 is identical in both cell types the ligand binding specificity and affinity differ on T cells vs. breast tumor cells.

Figure 3:
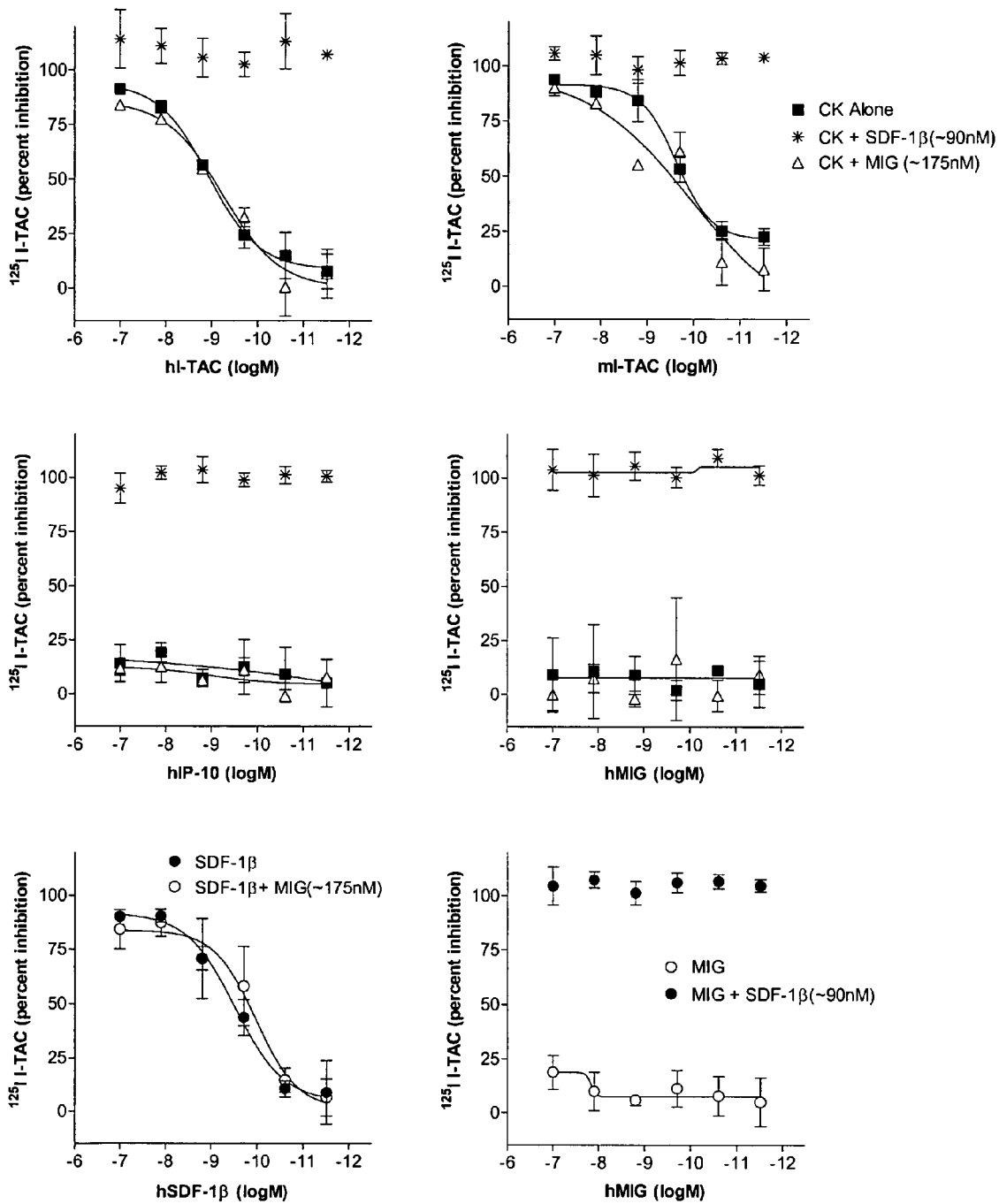
FIG. 3 illustrates $^{125}$I I-TAC binding on MCF-7 cells is not due to a classic CXCR3 binding interaction. The ability of $^{125}$I-TAC to compete with the indicated chemokines was examined in the presence of buffer only (solid squares), excess MIG (to inhibit any CXCR3-mediated binding; open triangles), or excess SDF-1α (asterisks).

We next investigated whether the I-TAC binding detected on MCF-7 cells could be CXCR3-mediated since CXCR3 has long been established as the principal receptor for I-TAC (Cole, K. E. et al. *J Exp Med* 187:2009-21. (1998)). To this end, $^{125}$I I-TAC binding was examined under conditions that would inhibit 'classic' CXCR3 mediated binding (i.e. binding of the reported CXCR3 ligands MIG, I-TAC and IP-10 to CXCR3) thus permitting 'classic' CXCR4 mediated binding (i.e. binding of the reported CXCR4 ligand SDF-1 to CXCR4), as well as the converse situation. MCF-7 cells were pre-incubated with either medium alone, medium containing excess MIG (~175 nM; to inhibit CXCR3-mediated binding) or medium containing excess SDF-1β (~90 nM; to inhibit CXCR4-mediated binding). I-TAC competed with $^{125}$I I-TAC for binding to the MCF-7 cells with an IC50 of 1 nM (FIG. 3) confirming that it is a high affinity ligand for this receptor on these cells. Similarly, cells first pre-incubated with excess MIG were then still able to give the same homologous I-TAC/$^{125}$I I-TAC binding curve again with an IC50 of 1 nM (FIG. 3). However, when cells were first pre-treated with excess SDF-1β all $^{125}$I I-TAC binding was inhibited (FIG. 3) suggesting that the observed $^{125}$I I-TAC binding on breast tumor cells is mediated by the SDF1 receptor expressed on these cells. Similarly, $^{125}$I I-TAC binding to MCF-7 cells was not inhibited when IP-10 was tested as the cold chemokine competitor. Again, pre-incubation with excess MIG did not effect this binding profile; however pre-incubation of the cells with SDF-1β completely inhibited $^{125}$I I-TAC binding. When the CXCR3 ligand MIG was tested as the cold competitor $^{125}$I I-TAC binding to the cell was not inhibited (FIG. 3). As expected from the DisplaceMax™ data represented in FIG. 1, SDF-1β competed with $^{125}$I I-TAC for binding to these cells with high affinity (IC50 of 1 nM). Pre-incubation of cells with excess MIG did not effect the SDF-1β/$^{125}$I I-TAC competition, again suggesting the binding detected is not mediated by CXCR3.

This hypothesis was examined further by PCR. Isolated mRNA used previously (described above) was used to probe for evidence of CXCR3 transcripts. While, IL-2 cultured lymphocytes expressed CXCR3; no other cell tested expressed CXCR3. The lack of detected CXCR3 expression by RT PCR supports data from FIG. 3, again suggesting that the I-TAC binding on MCF-7 cells is not CXCR3-mediated.

The altered anti-CXCR4 antibody reactivity as well as the altered ligand binding specificity and affinity led us to consider that this receptor was not classic CXCR4. There are a few 'orphan' chemokine receptors that have been identified, but for which the chemokine ligand has not been identified. We considered several orphan receptors. One such receptor is called RDC1 (herein referred to as CCX-CKR2). When the protein sequence for RDC1 is transfected into MDA MB 435s (a cell line that does not endogenously express CXCR4, CXCR3 or CCX-CKR2) the hallmark radioligand binding phenotype is recapitulated (FIG. 4). CCX-CKR2 expressed in MDA MB 435s binds to radiolabeled SDF-1. This binding is competed by the cold competitors SDF-1 and I-TAC.

Figure 5:
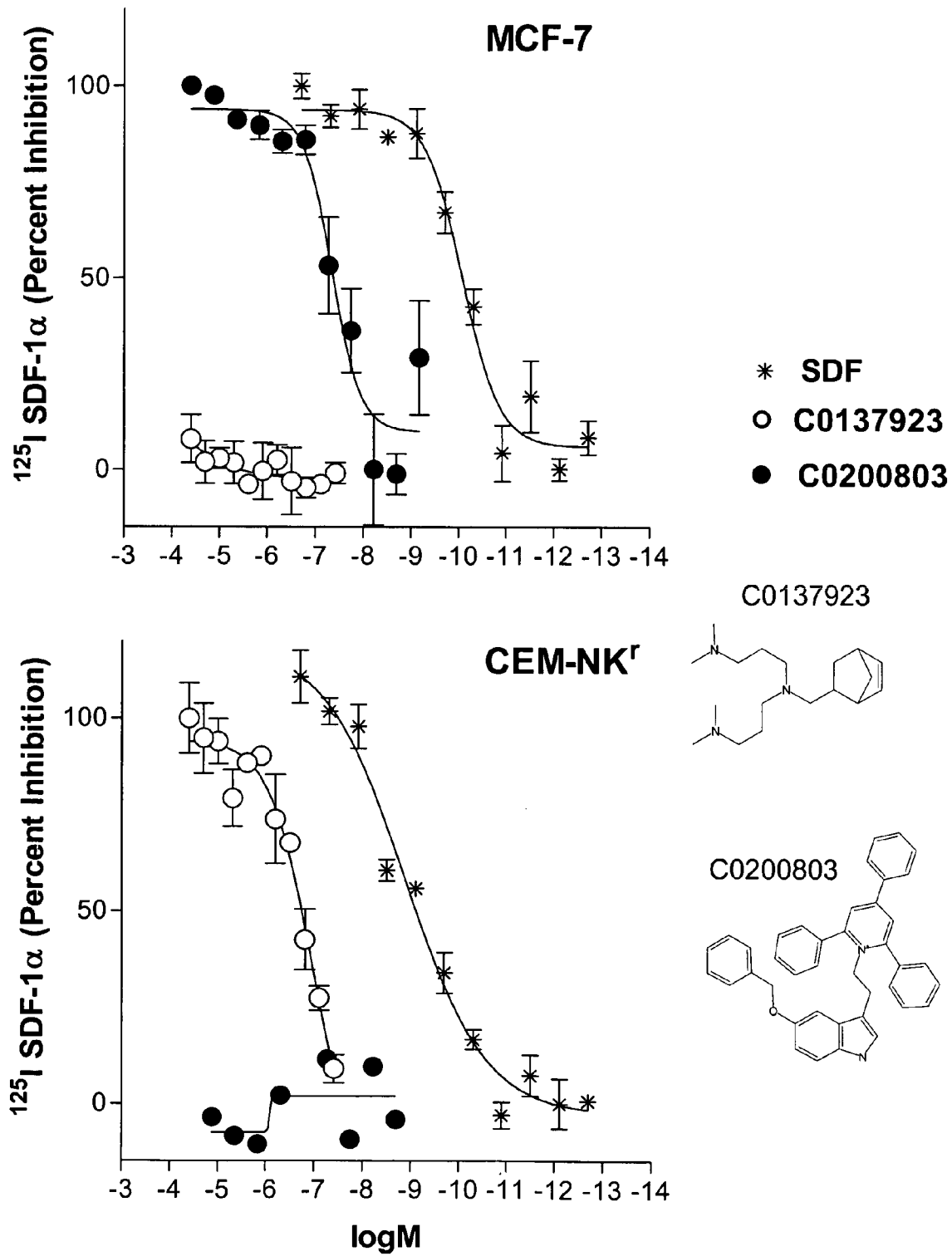
FIG. 5 illustrates competitive binding data. Two small molecules, CCX0803 (solid circles) and CCX7923 (open circles), compete specifically with $^{125}$I SDF-1α, on discrete cell types; no cross competition is detected. SDF-1α (asterisks) was also included as a cold competitor of $^{125}$I SDF-1α binding on both MCF-7 and CEM-NKr. Chemical structures of CCX0803 and CCX7923 are shown in the inset. The predicted $IC_{50}$ values of SDF-1α and CXCR4 antagonist competition are provided in the accompanying table.

In the effort to target this receptor with small molecular weight organic compound (SMC) therapeutics, we screened small molecules (nearly 135,000) using two high throughput screens: one designed to assess the CXCR4-mediated leukocyte SDF-1 binding phenotype and one to probe the CCX-CKR2-mediated breast cancer SDF-1 binding phenotype. The results of those screens indicated that clear pharmacologic discrimination of the two binding phenotypes was possible (FIG. 5). For example, the small molecule designated CCX0803 competes with $^{125}$I SDF-1α for binding to MCF-7 with an IC50 of 46 nM (FIG. 5), however, this small molecule does not inhibit $^{125}$I SDF-1α binding on CEM-NKr at all (FIG. 5). By contrast, a different small molecule antagonist, CCX7923, inhibits $^{125}$I SDF-1α binding to CEM-NKr with an IC50 of 106 nM (FIG. 5), but does not inhibit $^{125}$I SDF-1α binding on MCF-7 cells (FIG. 5). These two compounds reveal the marked and unambiguous pattern of non-reciprocal binding inhibition of ligands to the two receptors (breast tumor lines vs. leukocytes).

After initially determining that breast cancer cells exhibit a binding affinity for SDF-1 which is distinct from that seen on other non-tumor or non-cancerous tissue further studies were undertaken. These phenotyping studies (using antibody reactivity, ligand binding profile and pharmacologic discrimination, see methods detailed herein), have clearly shown that many cancer (or tumor) cell types also exhibit the binding affinity (e.g., antibody reactivity, ligand binding and pharmacologic discrimination) initially correlated with breast tumor cells and thus CCX-CKR2 expression. The following tumor cells were examined and exhibit the cancer-correlated binding affinity: human ovarian carcinoma, human cervical adenocarcinoma, human Burkitt's lymphoma, human mammary adenocarcinoma, human mammary ductal carcinoma, human glioblastoma, and mouse mammary tumor.

Tumors and other cancers are difficult to treat in part because of their rapid rate of cell growth. In this respect, tumors are known to share some growth characteristics with rapidly dividing early embryonic tissues. One school of thought suggests that tumors in the adult may represent 'revertants' to an embryonic growth phenotype. Both the SDF-1 and CXCR4 genetic knockout mice are embryonic lethal, suggesting that this ligand receptor pair is a critical component of growth and development. Approximately 50% of homozygous mutant SDF-1 embryos die perinatally by 18.5; the remaining homozygous littermates die within 1 hr of birth (Kishimoto, et al. *Nature* 382: 635-638 (1996)). Similarly, ~⅓ of the homozygous CXCR4 knock out mice die perinatally at E18.5 (Ma, et al *Proc. Natl. Acad. Sci. USA* 95:9448-9453 (1998)). In both the receptor and ligand knockouts defects in lymphopoiesis and myelopoiesis were observed. The fetal liver is the major site of hematopoiesis in the mouse at day 11 and continues as such until the first post-natal week. To this end we decided to examine the expression of CCX-CKR2 in this compartment. We examined CCX-CKR2 expression on wildtype mouse embryos at E17 (a point in development close to the time the knockout animals die) and E13 (a point in development distinct from the time the knockout animals die, yet after hematopoiesis begins).

In SDF-1 binding assays radiolabeled human-SDF-1 binds to E13 fetal liver cells and both SDF and I-TAC (mouse and human proteins) are able to compete with the radiolabeled tracer for binding. This altered ligand specificity as exemplified by I-TAC binding to the SDF-1 receptor is a hallmark of the binding phenotype we first correlated with cancer cells and have now demonstrated to be CCX-CKR2. Furthermore, CCX-CKR2 antagonists are able to compete with SDF-1 binding on E13 fetal liver; however CXCR4 antagonists do not.

Later in development, fetal liver cells at E17 express CXCR4, and these cells respond to SDF-1 by mobilizing intracellular calcium. CXCR4 antagonists inhibit this SDF-1 mediated calcium mobilization however, the CCX-CKR2 antagonists have no effect. Thus, these data suggest that wild-type fetal liver cells at E13 and E17 both express CXCR4, however, CCX-CKR2 is expressed early (E11) but not at later timepoints (E15).

Although the binding studies in embryonic mice models correlate well with data from human studies, preliminary experiments using mice which have a targeted disruption of the CXCR4 gene suggest that the SDF-1 and I-TAC binding profiles observed on embryonic day 13 (E13) fetal liver cells are unchanged. This provides further evidence that the gene encoding the polypeptide with the cancer-related SDF-1 binding affinity is not CXCR4.

Experiments also demonstrate that the CCX-CKR2 receptor can provide a stimulatory signal to growing tumor cells. Tumor cells can upregulate certain genes involved in cell cycle or transcription in response to SDF-1 stimulation. More importantly, if tumor cells are starved of serum in culture overnight they begin to go through apoptosis (cell death). When SDF-1 is added to supplement these cultures the cells are able to recover from the starvation as compared to untreated controls. Thus SDF-1 therefore serves as an anti-apoptotic signal. Cancer cells are often characterized as cells that have lost the ability to undergo apoptosis.

Example 2

This example demonstrates that the cancer-related binding phenotype discussed in Example 1 is mediated by CCX-CKR2 (previously known as the orphan receptor RDC1).

In general CCX-CKR2 is preferentially expressed on transformed cells. As displayed in Table 1 (left column), a variety of different cancer cells tested positive for expression of CCX-CKR2. In contrast, most normal (non-tumor) cells did not express CCX-CKR2. See, Table 1 (right column).

TABLE 1

| CCX-CKR2 positive | CCX-CKR2 negative |
| --- | --- |
| human Mammary Carcinoma (MCF-7, MDA MB 361) | normal human PBMC |
| human Glioblastoma (T98G) | human T cell leukemia (MOLT4, Jurkat, CEM-NKr) |
| human Prostate Carcinoma (LN Cap) | |
| human B cell Lymphoma (Raji, IM9) | unstimulated endothelial cells |
| human Ovarian Carcinoma (HeLa) | |
| human Lung Carcinoma (A549) | mouse thymus |
| | mouse lung |
| mouse Mammary carcimoma (4T1) | mouse spleen |
| mouse Pancreatic Epithelial cells, SV40 transformed (SVR) | mouse heart |
| | mouse PBL |
| mouse B cell Lymphoma (BCL1) | mouse liver |
| mouse normal kidney * | mouse total adult bone marrow |
| mouse normal brain * | mouse lineage negative adult bone marrow |
| mouse fetal liver (E11 through E13) | mouse fetal liver (E15 through birth) |
| activated endothelial cells | |

* expression on these organs is weak as determined by radioligand binding signal Nevertheless, there does appear to be a role for CCX-CKR2 in some normal cells. The CCX-CKR2 receptor is expressed for a period of time in fetal development. CCX-CKR2 is expressed on mouse fetal liver by the 11$^{th}$ day of embryogenesis (E11), but by E15 it is no longer detected (as determined by radiolabeled SDF1 binding and I-TAC displacement) as well as CCX-CKR2 transcripts detected by Northern analysis. In the adult mouse it is expressed in normal kidney. By comparison to the kidney expression, there is lower expression in normal brain. Because the examination is done with whole brain homogenates this low signal in the radioligand binding assay is consistent with a small population of cells in the brain expressing CCX-CKR2.

Figure 6:
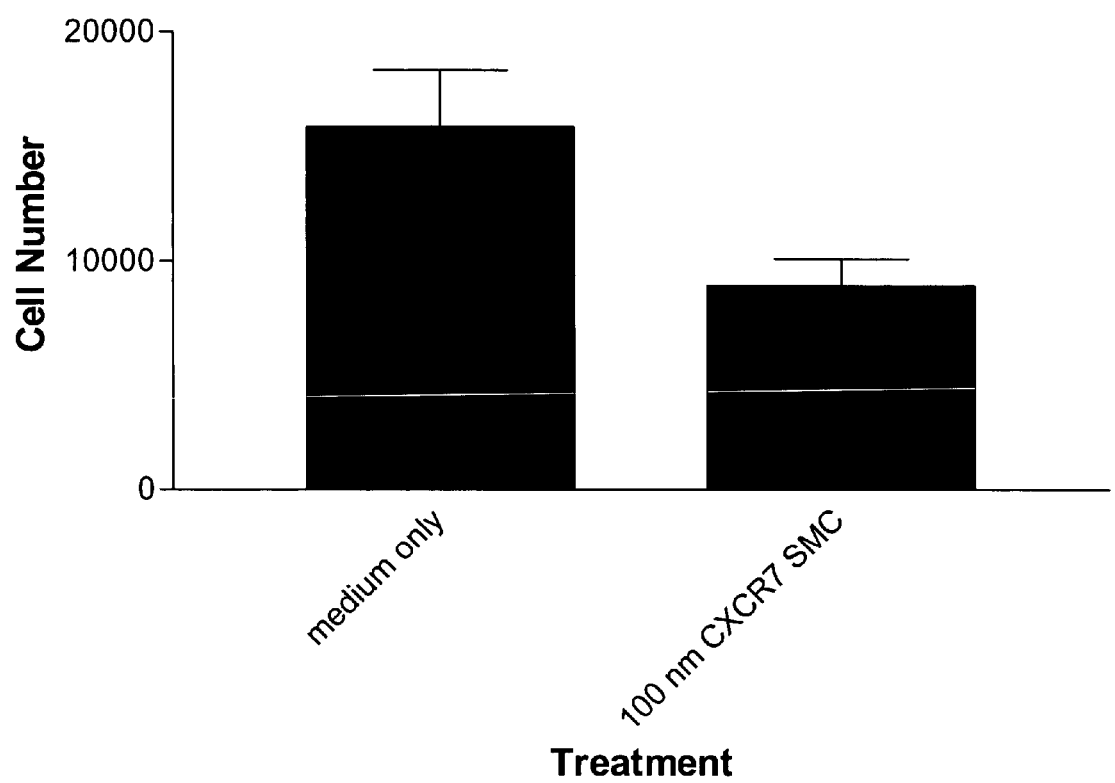
FIG. 6 illustrates the effect of treatment of mammary carcinoma cells, which express CCX-CKR2, with a small molecule CCX-CKR2 antagonist compared to cells not treated with the antagonist.

To further bolster the evidence of CCX-CKR2's role in cancer, we demonstrated that cancer cell growth can be inhibited by antagonizing CCX-CKR2 in cancer cells. Antagonism of CCX-CKR2 expressed on a mammary carcinoma by a CCX-CKR2 antagonist inhibited cell proliferation in vitro. Cells treated in vitro exhibited reduced cell growth over time as compared to untreated controls. See, FIG. 6.

Figure 7:
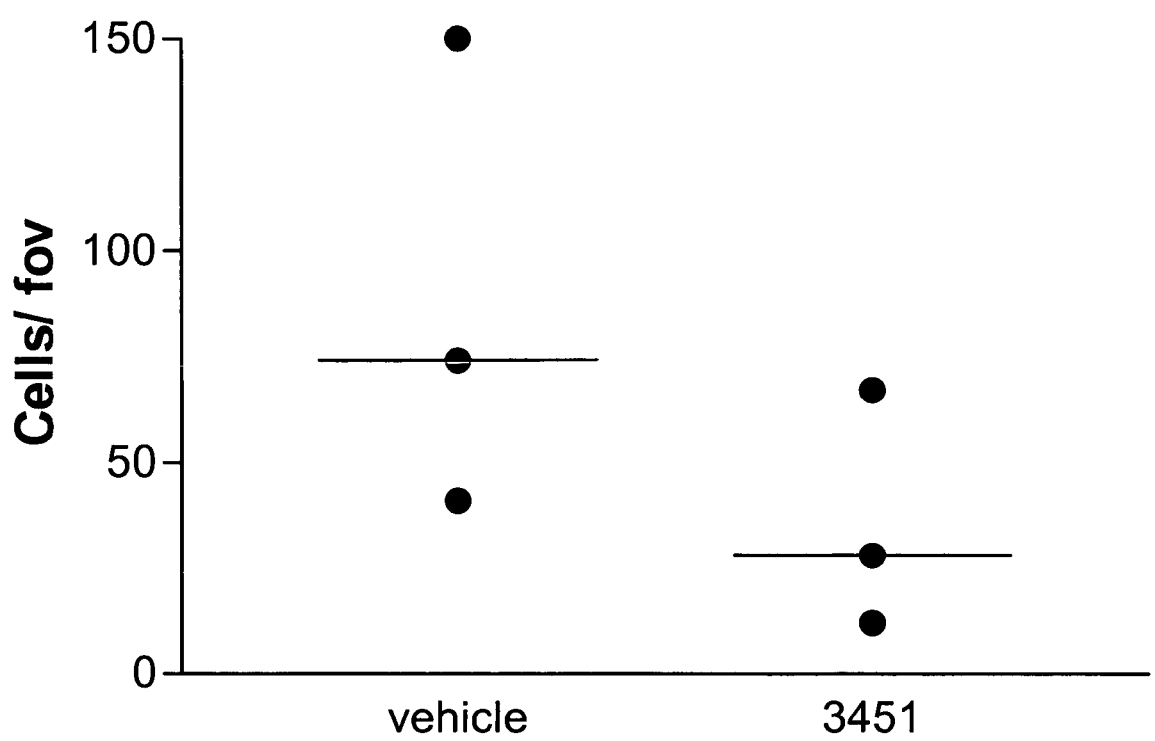
FIG. 7 illustrates that CCX-CKR2 antagonist 3451 (see, Table 1, Compound No. 49) inhibits adhesion of CCX-CKR2-expressing cells to a vascular endothelial monolayer.

CCX-CKR2 is also involved in adhesion. Leukocyte migration involves several steps including the adhesion of cells and subsequent emigration into a given tissue. In vitro static adhesion assays model this event. Monolayers of vascular endothelial cells are grown on a surface. Cells expressing CCX-CKR2 are then labeled with a fluorescent dye for visualization. When CCX-CKR2 cells are allowed to adhere to the endothelial surface many more CCX-CKR2 expressing cells attach to the endothelial layer than do a CCX-CKR2-cell control. Furthermore, the addition of a CCX-CKR2 antagonist inhibits the adhesion as compared to a vehicle-treated control. See, FIG. 7.

In vivo evidence further supports a role for CCX-CKR2 in tumor growth. Tumors form when human B cell lymphoma cells, which express CCX-CKR2, are injected into immunodeficient mice. Treatment of these mice with CCX-CKR2 antagonists inhibited vascularized tumor formation. In one such study, 1 of 17 mice treated with a CCX-CKR2 antagonist developed an encapsulated, vascularized tumor while 11 of 17 mice in the vehicle treated group developed encapsulated vascularized tumors. These data suggest that CCX-CKR2 may be involved in the ability of a tumor to differentiate and establish a vascular bed and provides evidence that antagonism of CCX-CKR2 is a useful cancer therapy.

Figure 8:
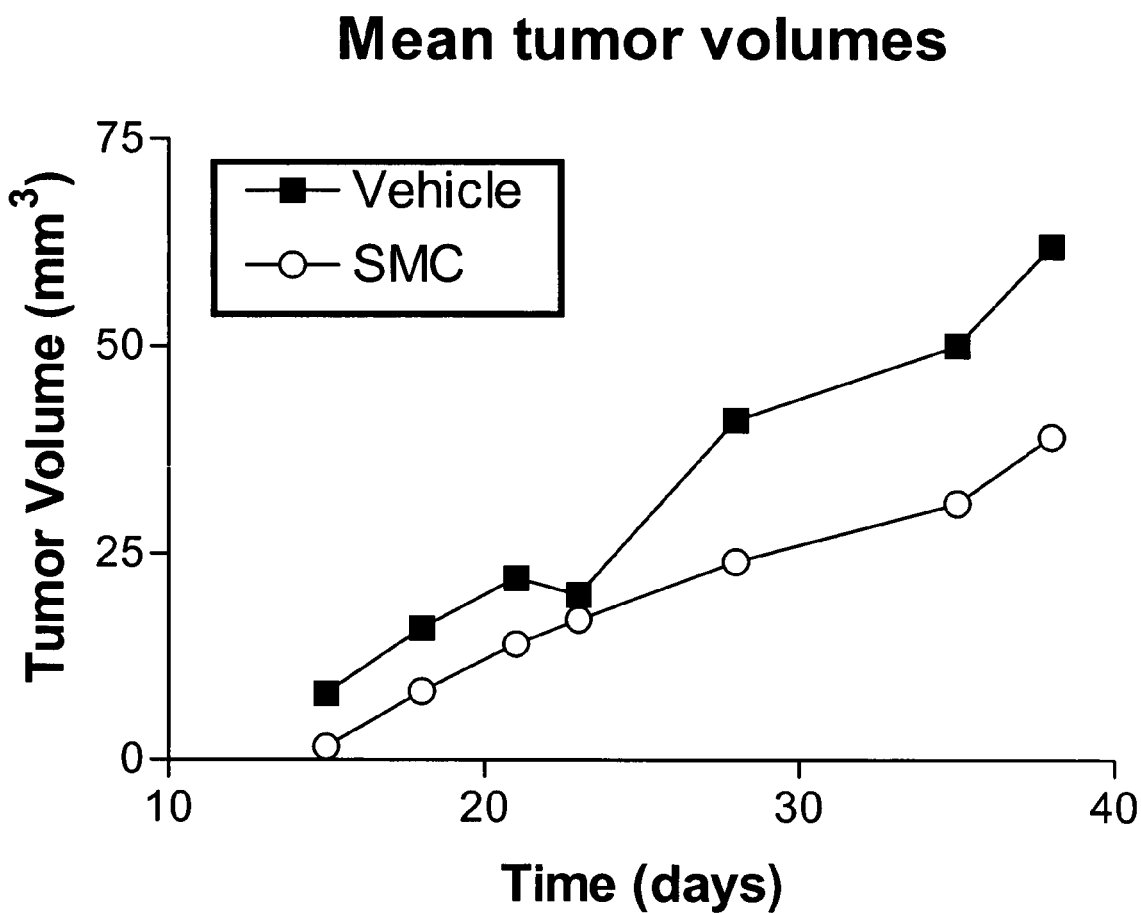
FIG. 8 illustrates that antagonism of CCX-CKR2 on mammary carcinoma cells reduces tumor volume.

The effect of antagonism of CCX-CKR2 was also tested in a breast cancer model. In a model of breast tumor growth, immunodeficient mice were injected with a human mammary carcinoma. Tumor measurements were made 3 times a week and volumes were plotted. Mice that were treated with a CCX-CKR2 antagonist exhibited reduced tumor volume as compared to the vehicle control group, demonstrating that CCX-CKR2 has a role in tumor growth. See, FIG. 8.

Example 3

This example demonstrates that CCX-CKR2 promotes cell survival by reducing apoptosis.

Interactions between chemokines and chemokine receptors are typically assessed by measuring intracellular calcium mobilization and chemotaxis. However, CCX-CKR2 does not produce a transient calcium mobilization or cause cells to migrate in response to its ligands CXCL12 or CXCL11. Cells expressing CCX-CKR2 do however exhibit increased adhesion to activated endothelial cell monolayers. Furthermore, under conditions of low serum supplementation of the culture medium (i.e. 1% instead of the regular 10%), the recovery of live adherent cells after three days was much greater for CCX-CKR2-MDA MB 435s transfectants (designated CCX-CKR2 435s) versus untransfected WT cells (WT 435s). Consistent with this observation, the frequency of dead cells recovered in the supernatant collected from these cultures was much greater for WT versus CCX-CKR2-transfectants. This effect could be visualized fluorescently using the DNA intercalating dye 7AAD (7 aminoactinomycin D). CCX-CKR2-435s transfectants or wild type 435s cells were grown in different serum concentrations, then harvested and incubated with 7AAD (1 ug/ml in DMSO) for 15-30 minutes at room temperature. FACS analysis revealed many more dead/apoptotic cells (i.e. 7AAD-positive) in wild-type 435s cells versus CCX-CKR2-435s transfectants.

We have now extended these findings in a series of experiments where cultured CCX-CKR2-transfectants or untransfected WT cells are co-stained with Annexin which detects only apoptotic cells, and propridium iodide (PI) which detects dead cells but not apoptotic cells. This approach readily identifies the proportion of apoptotic cells in a cell population, as demonstrated using agents known to induce cellular apoptosis, e.g. camptothecin (CMP), or TNFalpha plus cycloheximide (CHX), and which provide excellent controls in these assays.

Using this assay, we measured the development of apoptotic cells over time of CCX-CKR2-435s transfectants or wild type 435s cells grown either in optimal (10%) or limiting (1%) serum. Both cell types grown in 10% serum showed excellent viability over a 4 day culture period. In contrast, WT cells grown in 1% serum showed a dramatic reduction in viable cells after 3 and 4 days of culture. Co-staining with Annexin and PI revealed this reflected development of both apoptoic and dead cells. Interestingly, CCX-CKR2-435s cells grown in 1% serum showed excellent viability over the same 4 day culture period, suggesting that the introduction of CCX-CKR2 into 435s protected these cells from the rapid cellular apoptosis occurring under conditions of sub-optimal serum supplementation.

Identical results were obtained in a second experiment using the same CCX-CKR2-435s transfectant, and in addition a separate non-clonal population of 435s cells transfected with CCX-CKR2. The latter results indicated that the apoptosis-sparing property of the initial clonal transfectant resulted from CCX-CKR2 expression rather than a particular aberration of that one transfectant clone.

Example 4

This example demonstrates that CCX-CKR2 mediated phosphorylation of p44/42 MAPK (ERK1 and ERK2).

CCX-CR2 is an unusual receptor in that ligand binding (e.g., by ITAC or SDF1) does not result in the mobilization of calcium that is typical of many chemokine receptors. This prompted an evaluation of other potential signaling pathways, including an investigation into whether CCX-CR2 activity was mediated through ERK phosphorylation. Experiments conducted with lysates from a MCF7 cell line expressing CCX-CR2 that was stimulated with either ITAC or SDF1 demonstrated that there is a ligand-dependent phosphorylation of ERK1 and ERK2 (sometimes also referred to in the literature as p44/42 MAPK). Phosphorylated ERK1 and ERK2 was detected by Western blot analysis, with lysates from the MCF7 cell line initially subjected to electrophoresis to separate proteins in the lysate. Phosphorylated ERK1 and ER2 on the electrophoretic gel were detected by probing with antibodies specific for the phosphorylated form of these proteins. These antibodies are available from Cell Signaling Technologies of Beverly, Mass.

Similar experiments were conducted with Hela cells expressing CCX-CR2. The same results were obtained when these cells were stimulated with either ITAC or SDF1.

Since ITAC and SDF1 bind to other chemokine receptors, e.g., CXCR3 in the case of ITAC, and CXCR4 in the case of SDF1, it was important to consider the potential contribution of these receptors to the ERK phosphorylation induced by these ligands in MCF7 cells. FACS analysis of MCF7 cells using antibodies specific for CXCR3 or CXCR4 revealed a complete absence of these receptors on MCF7 cells. Positive controls using cell lines expressing CXCR3 or CXCR4 validated that the antibodies used in these experiments could bind these receptors. These data thus indicate that binding ligands such as ITAC or SDF1 to CCX-CR2 causes intracellular signaling via a phosphorylation of ERK, which likely results in the activation of additional downstream components. The finding that CCX-CR2 mediates the phosphorylation of ERK1 and ERK2 indicates that CCX-CR2 is associated with a variety of biological processes because ERK phosphorylation has been demonstrated to mediate the regulation of cell growth and cell differentiation.

Example 5

This example demonstrates that cellular expression of CCX-CKR2 causes induction of numerous regulatory proteins.

As an alternative approach to investigating CCX-CKR2-mediated signalling events, supernatants collected from CCX-CKR2 transfected MDA MB 435s cells were compared to supernatants collected from wild-type MDA MB 435s (435s) cells, evaluated by specific ELISA assays for the presence of a large family of secreted proteins. 435s cells expressing CCX-CKR2 produced substantially greater quantities of GM-CSF, RANTES, MCP-1, TIMP-1, and MMP3 than wild-type 435s cells, especially when grown under limiting serum conditions. Interestingly, all these factors have been reported to be involved in growth, vascular remodeling and chemotaxis related to tumorigenesis. They may also be involved in the apoptosis-sparing phenotype of CCX-CKR2 described above.

Example 6

This example demonstrates that siRNA-based inhibition of CCX-CKR2.

We obtained SMARTpool™ siRNA (Dharmacon) specific for either CXCR4 or CCX-CKR2. SMARTpool™ siRNA is a pool of four different siRNA sequences, each targeting a different region of the specified mRNA. These siRNA pools were tested in HeLa cells. CXCR4 expression was assessed by 12G5 or 173 Mab staining and FACS, while CCX-CKR2 expression was measured in a binding assay using $^{125}$I-SDF1. CXCR4 is expressed on HeLa cells in a conformation that does not exhibit detectable $^{125}$I-SDF1 binding, thus allowing for detection of CCX-CKR2 expression. CCX-CKR2 SMARTpool™ siRNA (25-100 nM) effected significant ($\geq$50%) inhibition of $^{125}$I-SDF1 binding, while CXCR4 SMARTpool™ siRNA did not. Similar results were obtained with 293-CCX-CKR2 transfectants.

In addition, the following 3 siRNA sequences were each found to reduce SDF-1 binding when introduced into cells at a concentration as low as 4 nM:

```
siRNA #1: GCCGTTCCCTTCTCCATTATT   (SEQ ID NO: 12)
siRNA #2: GAGCTCACGTGCAAAGTCATT   (SEQ ID NO: 13)
siRNA #3: GACATCAGCTGGCCATGCATT.  (SEQ ID NO: 14)
```

Example 7

This example demonstrates expression of CCX-CKR2 in the brain.

CCX-CKR2 is expressed on a large number of tumor cell lines, but in few normal tissues. One exception to the latter pattern was provided by the demonstration in binding studies that brain cells from normal adult mice expressed CCX-CKR2. To extend these observations, in situ hybridization studies were performed using a CCX-CKR2-specific probe to localize the region of CCX-CKR2 expression within the brain. Brain samples were collected from normal adult mice, and fixed with 4% PFA in PBS overnight at 4° C., followed by 30% sucrose in PBS overnight at 4° C. Tissues were then embedded in OCT, cut in 20 um slices, then collected on superfrost plus slides. For in situ hybridization studies, antisense and sense riboprobes were prepared by in vitro transcription, respectively, with T7 and SP6 RNA Polymerase using DIG cRNA labeling kit (Roche) after linearization. The 20 um cryosections were fixed in fresh 4% PFA, followed by protease K treatment (2 ug/ml for 20 min at 37° C.). The slides are pre-hybridized at 55° C. for 1 hour, and then hybridized at 55° C. O/N in sealed containers. Slides were then washed with 50% formamide, 5×SSC pH4.5 and 1% SDS at 65° C., followed by blocking with 5% sheep serum for 1 hour and incubation with 1:1000 anti-Dig antibody in 1% sheep serum for O/N at 4° C. Slides were washed with TBST, and detected with NBT/BCIP.

The results clearly demonstrate strong expression of CCX-CKR2 by neurons within the cerebellum, hippocampus and cortex. There is little or no detectable expression in areas that contain glial cells such as the white matter tracts in the cerebellum, and the corpus callosum. Purkinje cells showed uniformly strongly positive signal and a subset of the granule cells in the internal granule cell layer showed positive signal. In addition, the cortex is generally quite positive, and individual neurons within the cortex showed clear positive staining. The hippocampus showed strong CCX-CKR2 signal in neurons of the dentate gyrus and CA1-3. In addition, the overlying cortexi was also positive.

These data provide some insight regarding the potential relevance of CCX-CKR2 to brain tumors. CCX-CKR2 is not expressed in the ventricular zone cells, or glial cells, where astrocytomas are believed to originate. In contrast, there is some expression in what appears to be a subset of cerebellar granule cells, the cell type from which medulloblastomas derive. The expression profile for CCX-CKR2 is very different from that seen for the other SDF-1 receptor CXCR4, as described by others.

Example 8

This example demonstrates the efficacy of a CCX-CKR2 ligand competitor in a mouse xenograft model of lung carcinoma.

Lung carcinoma is the leading cancer cause of death in the US. CCX-CKR2 is expressed on lung carcinoma as well as in activated endothelium. The effects of administration of a CCX-CKR2 ligand competitor, a 700 series compound, in a xenograft model of lung carcinoma was evaluated.

In the lung carcinoma xenograft study, A549 tumor fragments (30-40 mg) were implanted into the sub cutaneous space in nude mice. Tumors were permitted to grow until approximately 150 mg in size (between 100 and 200 mg) at which point mice were enrolled in the study and treatment began. Mice were treated with the CCX-CKR2 ligand competitor (25 mpk; sc administration, Q1D) or the vehicle control. Melphalan was included as the positive control (9 mpk/dose, ip administration, Q4Dx3). Tumors were measured twice weekly with a caliper in two dimensions and converted to tumor mass using the formula for a prolate ellipsoid (a×b$^2$/2), where a is the longer dimension and b is the shorter dimension, and assuming unit density (1 mm$^3$=1 mg). Body weights were also measured twice weekly to assess any adverse effects of compound dosing. Antitumor activity was assessed by the delay in tumor growth of the treated group in comparison to the vehicle-treated control group.

The mice receiving the competitor exhibited reduced tumor load compared to the vehicle treated group. This difference in tumor volume was statistically significant between these groups and represents a 32% reduction in average tumor volume. Melphalan also reduced tumor volume with a 60% reduction in average tumor volume. Additionally, the daily treatment with the competitor was well tolerated in this study as determined by the weight gain in the compound treated animals consistent with that of vehicle treated mice.

Tumor weights were assessed on the final day of compound treatment (day 49). Mice treated with the CCX-CKR2 competitor exhibited tumors that were statistically smaller than those in the vehicle control group. Similarly, mice receiving Melphalan also had significantly smaller tumors than the vehicle treated group.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of treating a cancer in an individual, wherein cancer cells in the individual express CCX-CKR2, the method comprising administering to the individual a therapeutically effective amount of an antibody that binds to the extracellular domain of the amino acid sequence of SEQ ID NO:2.

2. The method of claim 1, wherein the antibody is identified by a method comprising
   contacting a plurality of antibodies to a CCX-CKR2 polypeptide comprising an extracellular domain at least 95% identical to an extracellular domain of the amino acid sequence of SEQ ID NO:2, or a SDF1 or I-TAC-binding fragment thereof; and
   selecting an antibody that competes with I-TAC or SDF-1 for binding to the CCX-CKR2 polypeptide or fragment thereof, thereby identifying an antibody that treats cancer.

3. The method of claim 1, wherein the cancer is not Kaposi's sarcoma, multicentric Castleman's disease or AIDS-associated primary effusion lymphoma.

4. The method of claim 1, wherein tumor formation is inhibited.

5. The method of claim 1, wherein tumor volume is reduced.

6. The method of claim 1, wherein the cancer comprises a mammary carcinoma.

7. The method of claim 1, wherein the cancer comprises a B cell lymphoma.

8. The method of claim 1, wherein the cancer comprises a lung carcinoma.

9. The method of claim 1, wherein the cancer is selected from the group consisting of mammary carcinoma, glioblastoma, prostate carcinoma, B cell lymphoma, ovarian carcinoma, and lung carcinoma.

10. The method of claim 1, wherein the antibody is identified by a method comprising
    contacting a plurality of antibodies to a CCX-CKR2 polypeptide comprising an extracellular domain of the amino acid sequence of SEQ ID NO:2; and
    selecting an antagonistic antibody that competes with I-TAC or SDF-1 for binding to the CCX-CKR2 polypeptide, thereby identifying an antibody that treats cancer.

* * * * *

SEQUENCE LISTING

```
<160> NUMBER OF SEQ ID NOS: 14

<210> SEQ ID NO 1
<211> LENGTH: 1089
<212> TYPE: DNA
<213> ORGANISM: Homo sapiens
<220> FEATURE:
<223> OTHER INFORMATION: G-protein coupled receptor (GPCR) CCX-CKR2
      (RDC1) coding sequence

<400> SEQUENCE: 1
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcggc agcattttct tcctcacgtg catgagcgtg     420
gaccgctacc tctccatcac ctacttcacc aacaccccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa aacagggctc    1020
accaagctca tcgatgcctc cagagtctca gagacggagt actctgcctt ggagcagagc    1080
accaaatga                                                            1089
```

```
<210> SEQ ID NO 2
<211> LENGTH: 362
<212> TYPE: PRT
<213> ORGANISM: Homo sapiens
<220> FEATURE:
<223> OTHER INFORMATION: G-protein coupled receptor (GPCR) CCX-CKR2
      (RDC1)

<400> SEQUENCE: 2
```

Met Asp Leu His Leu Phe Asp Tyr Ser Glu Pro Gly Asn Phe Ser Asp
 1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
     50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

```
<210> SEQ ID NO 3
<211> LENGTH: 1089
<212> TYPE: DNA
<213> ORGANISM: Homo sapiens
<220> FEATURE:
<223> OTHER INFORMATION: G-protein coupled receptor (GPCR) CCX-CKR2.2
      coding sequence

<400> SEQUENCE: 3
atggatctgc acctcttcga ctacgccgag ccaggcaact tctcggacat cagctggcca      60
tgcaacagca gcgactgcat cgtggtggac acggtgatgt gtcccaacat gcccaacaaa     120
agcgtcctgc tctacacgct ctccttcatt tacatttttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg cctcaccat cccagtctgg      300 gtggtcagtc tcgtgcagca caaccagtgg cccatgggcg agctcacgtg caaagtcaca     360
cacctcatct tctccatcaa cctcttcagc ggcattttct tcctcacgtg catgagcgtg     420
gaccgctacc tctccatcac ctacttcacc aacaccccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa aacagggctc    1020
accaagctca tcgatgcctc cagagtgtcg agacggagt actccgcctt ggagcaaaac    1080
gccaagtga                                                            1089

<210> SEQ ID NO 4
<211> LENGTH: 362
<212> TYPE: PRT
<213> ORGANISM: Homo sapiens
<220> FEATURE:
<223> OTHER INFORMATION: G-protein coupled receptor (GPCR) CCX-CKR2.2

<400> SEQUENCE: 4

Met Asp Leu His Leu Phe Asp Tyr Ala Glu Pro Gly Asn Phe Ser Asp
  1               5                  10                  15

Ile Ser Trp Pro Cys Asn Ser Ser Asp Cys Ile Val Val Asp Thr Val
                 20                  25                  30

Met Cys Pro Asn Met Pro Asn Lys Ser Val Leu Leu Tyr Thr Leu Ser
             35                  40                  45

Phe Ile Tyr Ile Phe Ile Phe Val Ile Gly Met Ile Ala Asn Ser Val
         50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110
```

Gly Glu Leu Thr Cys Lys Val Thr His Leu Ile Phe Ser Ile Asn Leu
        115                 120                 125

Phe Ser Gly Ile Phe Phe Leu Thr Cys Met Ser Val Asp Arg Tyr Leu
        130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
        180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
        210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
                260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
        290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
        340                 345                 350

Glu Tyr Ser Ala Leu Glu Gln Asn Ala Lys
        355                 360

<210> SEQ ID NO 5
<211> LENGTH: 1089
<212> TYPE: DNA
<213> ORGANISM: Homo sapiens
<220> FEATURE:
<223> OTHER INFORMATION: G-protein coupled receptor (GPCR) CCX-CKR2.3
      coding sequence

<400> SEQUENCE: 5
atggatctgc atctcttcga ctactcagag ccagggaact tctcggacat cagctggcca    60
tgcaacagca gcgactgcat cgtggtggac acggtgatgt gtcccaacat gcccaacaaa    120
agcgtcctgc tctacacgct ctccttcatt tacattttca tcttcgtcat cggcatgatt    180
gccaactccg tggtggtctg ggtgaatatc caggccaaga ccacaggcta tgacacgcac    240
tgctacatct tgaacctggc cattgccgac ctgtgggttg tcctcaccat cccagtctgg    300
gtggtcagtc tcgtgcagca caaccagtgg cccatgggcg agctcacgtg caaagtcaca    360
cacctcatct tctccatcaa cctcttcggc agcattttct tcctcacgtg catgagcgtg    420
gaccgctacc tctccatcac ctacttcacc aacacccccca gcagcaggaa gaagatggta    480
cgccgtgtcg tctgcatcct ggtgtggctg ctggccttct gcgtgtctct gcctgacacc    540
tactacctga agaccgtcac gtctgcgtcc aacaatgaga cctactgccg gtccttctac    600

```
cccgagcaca gcatcaagga gtggctgatc ggcatggagc tggtctccgt tgtcttgggc    660
tttgccgttc ccttctccat tgtcgctgtc ttctacttcc tgctggccag agccatctcg    720
gcgtccagtg accaggagaa gcacagcagc cggaagatca tcttctccta cgtggtggtc    780
ttccttgtct gctggttgcc ctaccacgtg gcggtgctgc tggacatctt ctccatcctg    840
cactacatcc ctttcacctg ccggctggag cacgccctct tcacggccct gcatgtcaca    900
cagtgcctgt cgctggtgca ctgctgcgtc aaccctgtcc tctacagctt catcaatcgc    960
aactacaggt acgagctgat gaaggccttc atcttcaagt actcggccaa aacagggctc   1020
accaagctca tcgatgcctc cagagtctca gagacggagt actctgcctt ggagcagagc   1080
accaaatga                                                          1089
```

```
<210> SEQ ID NO 6
<211> LENGTH: 362
<212> TYPE: PRT
<213> ORGANISM: Homo sapiens
<220> FEATURE:
<223> OTHER INFORMATION: G-protein coupled receptor (GPCR) CCX-CKR2.3

<400> SEQUENCE: 6
```

```
Met Asp Leu His Leu Phe Asp Tyr Ser Glu Pro Gly Asn Phe Ser Asp
 1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
     50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Val Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270
```

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
            290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
            325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
            355                 360

<210> SEQ ID NO 7
<211> LENGTH: 1089
<212> TYPE: DNA
<213> ORGANISM: Homo sapiens
<220> FEATURE:
<223> OTHER INFORMATION: G-protein coupled receptor (GPCR) CCX-CKR2.4
      coding sequence

<400> SEQUENCE: 7
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcggc agcattttct tcctcacgtg catgagcgtg     420
gaccgctacc tctccatcac ctacttcacc aacacccca gcagcaggaa gagatggta      480
cgccgtgtcg tctgcatcct ggtgtggctg ctggcctct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa acagggctc    1020
accaagctca cgatgcctc cagagtctca gagacggagt actctgcctt ggagcagagc    1080
accaaatga                                                             1089

<210> SEQ ID NO 8
<211> LENGTH: 362
<212> TYPE: PRT
<213> ORGANISM: Homo sapiens
<220> FEATURE:
<223> OTHER INFORMATION: G-protein coupled receptor (GPCR) CCX-CKR2.4

<400> SEQUENCE: 8

Met Asp Leu His Leu Phe Asp Tyr Ser Glu Pro Gly Asn Phe Ser Asp

|  1 | | | 5 | | | 10 | | | 15 | |
|---|---|---|---|---|---|---|---|---|---|---|

Ile Ser Trp Pro Cys Asn Ser Ser Asp Cys Ile Val Val Asp Thr Val
                20                      25                      30

Met Cys Pro Asn Met Pro Asn Lys Ser Val Leu Leu Tyr Thr Leu Ser
        35                      40                      45

Phe Ile Tyr Ile Phe Ile Phe Val Ile Gly Met Ile Ala Asn Ser Val
        50                      55                      60

Val Val Trp Val Asn Ile Gln Ala Lys Thr Thr Gly Tyr Asp Thr His
65                      70                      75                      80

Cys Tyr Ile Leu Asn Leu Ala Ile Ala Asp Leu Trp Val Val Leu Thr
                85                      90                      95

Ile Pro Val Trp Val Val Ser Leu Val Gln His Asn Gln Trp Pro Met
                100                     105                     110

Gly Glu Leu Thr Cys Lys Val Thr His Leu Ile Phe Ser Ile Asn Leu
                115                     120                     125

Phe Gly Ser Ile Phe Phe Leu Thr Cys Met Ser Val Asp Arg Tyr Leu
        130                     135                     140

Ser Ile Thr Tyr Phe Thr Asn Thr Pro Ser Ser Arg Lys Lys Met Val
145                     150                     155                     160

Arg Arg Val Val Cys Ile Leu Val Trp Leu Leu Ala Phe Cys Val Ser
                165                     170                     175

Leu Pro Asp Thr Tyr Tyr Leu Lys Thr Val Thr Ser Ala Ser Asn Asn
                180                     185                     190

Glu Thr Tyr Cys Arg Ser Phe Tyr Pro Glu His Ser Ile Lys Glu Trp
                195                     200                     205

Leu Ile Gly Met Glu Leu Val Ser Val Val Leu Gly Phe Ala Val Pro
        210                     215                     220

Phe Ser Ile Ile Ala Val Phe Tyr Phe Leu Leu Ala Arg Ala Ile Ser
225                     230                     235                     240

Ala Ser Ser Asp Gln Glu Lys His Ser Ser Arg Lys Ile Ile Phe Ser
                245                     250                     255

Tyr Val Val Val Phe Leu Val Cys Trp Leu Pro Tyr His Val Ala Val
                260                     265                     270

Leu Leu Asp Ile Phe Ser Ile Leu His Tyr Ile Pro Phe Thr Cys Arg
        275                     280                     285

Leu Glu His Ala Leu Phe Thr Ala Leu His Val Thr Gln Cys Leu Ser
        290                     295                     300

Leu Val His Cys Cys Val Asn Pro Val Leu Tyr Ser Phe Ile Asn Arg
305                     310                     315                     320

Asn Tyr Arg Tyr Glu Leu Met Lys Ala Phe Ile Phe Lys Tyr Ser Ala
                325                     330                     335

Lys Thr Gly Leu Thr Lys Leu Ile Asp Ala Ser Arg Val Ser Glu Thr
                340                     345                     350

Glu Tyr Ser Ala Leu Glu Gln Ser Thr Lys
                355                     360

```
<210> SEQ ID NO 9
<211> LENGTH: 1089
<212> TYPE: DNA
<213> ORGANISM: Homo sapiens
<220> FEATURE:
<223> OTHER INFORMATION: G-protein coupled receptor (GPCR) CCX-CKR2.5
      coding sequence

<400> SEQUENCE: 9
```

-continued

```
atggatctgc atctcttcga ctactcagag ccagggaact tctcggacat cagctggccg      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcagc agcattttct tcctcacgtg catgagcgtg     420
gaccgctacc tctccatcac ctacttcacc aacaccccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggttgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa acagggctc    1020
accaagctca tcgatgcctc cagagtctca gagacggagt actccgcctt ggagcagagc    1080
accaaatga                                                            1089
```

<210> SEQ ID NO 10
<211> LENGTH: 362
<212> TYPE: PRT
<213> ORGANISM: Homo sapiens
<220> FEATURE:
<223> OTHER INFORMATION: G-protein coupled receptor (GPCR) CCX-CKR2.5

<400> SEQUENCE: 10

```
Met Asp Leu His Leu Phe Asp Tyr Ser Glu Pro Gly Asn Phe Ser Asp
  1               5                  10                  15
Ile Ser Trp Pro Cys Asn Ser Ser Asp Cys Ile Val Val Asp Thr Val
                 20                  25                  30
Met Cys Pro Asn Met Pro Asn Lys Ser Val Leu Leu Tyr Thr Leu Ser
             35                  40                  45
Phe Ile Tyr Ile Phe Ile Phe Val Ile Gly Met Ile Ala Asn Ser Val
         50                  55                  60
Val Val Trp Val Asn Ile Gln Ala Lys Thr Thr Gly Tyr Asp Thr His
 65                  70                  75                  80
Cys Tyr Ile Leu Asn Leu Ala Ile Ala Asp Leu Trp Val Val Leu Thr
                 85                  90                  95
Ile Pro Val Trp Val Val Ser Leu Val Gln His Asn Gln Trp Pro Met
            100                 105                 110
Gly Glu Leu Thr Cys Lys Val Thr His Leu Ile Phe Ser Ile Asn Leu
        115                 120                 125
Phe Ser Ser Ile Phe Phe Leu Thr Cys Met Ser Val Asp Arg Tyr Leu
    130                 135                 140
Ser Ile Thr Tyr Phe Thr Asn Thr Pro Ser Ser Arg Lys Lys Met Val
145                 150                 155                 160
Arg Arg Val Val Cys Ile Leu Val Trp Leu Leu Ala Phe Cys Val Ser
```

```
                        165                 170                 175
Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:chemokine
      receptor second extracellular loop

<400> SEQUENCE: 11

Asp Arg Tyr Leu Ala Ile Val His Ala
  1               5

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:small
      interfering RNA (siRNA) #1

<400> SEQUENCE: 12
gccgttccct tctccattat t                                          21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:small
      interfering RNA (siRNA) #2

<400> SEQUENCE: 13
gagctcacgt gcaaagtcat t                                          21
```

```
<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:small
      interfering RNA (siRNA) #3

<400> SEQUENCE: 14
gacatcagct ggccatgcat t                                              21
```